US012599446B2

(12) United States Patent
Shelton, IV et al.

(10) Patent No.: US 12,599,446 B2
(45) Date of Patent: Apr. 14, 2026

(54) ROBOTIC SURGICAL SYSTEM WITH REMOVABLE PORTION AND METHOD OF DISASSEMBLING SAME

(71) Applicant: Cilag GmbH International, Zug (CH)

(72) Inventors: Frederick E. Shelton, IV, Hillsboro, OH (US); Jacqueline C. Aronhalt, Loveland, OH (US); Taylor W. Aronhalt, Loveland, OH (US); David A. Bruns, Kettering, OH (US); Matthew E. Derrico, Milford, OH (US); Kevin M. Fiebig, Cincinnati, OH (US); Cameron D. McLain, Deer Park, OH (US)

(73) Assignee: Cilag GmbH International, Zug (CH)

( * ) Notice: Subject to any disclaimer, the term of this patent is extended or adjusted under 35 U.S.C. 154(b) by 677 days.

(21) Appl. No.: 17/854,104

(22) Filed: Jun. 30, 2022

(65) Prior Publication Data

US 2024/0000526 A1     Jan. 4, 2024

(51) Int. Cl.
| | |
|---|---|
| *A61B 34/32* | (2016.01) |
| *A61B 17/00* | (2006.01) |
| *A61B 17/32* | (2006.01) |
| *A61B 50/30* | (2016.01) |
| *A61B 90/50* | (2016.01) |

(52) U.S. Cl.
CPC ...... *A61B 34/32* (2016.02); *A61B 17/320068* (2013.01); *A61B 50/30* (2016.02); *A61B 90/50* (2016.02); *A61B 2017/00477* (2013.01); *A61B 2017/320074* (2017.08)

(58) Field of Classification Search
CPC ......... A61B 34/32; A61B 50/30; A61B 90/50; A61B 17/320068; A61B 2017/320074; A61B 2017/00477; A61B 34/30
See application file for complete search history.

(56) References Cited

U.S. PATENT DOCUMENTS

| | | | |
|---|---|---|---|
| 7,354,440 | B2 | 4/2008 | Truckai et al. |
| 7,381,209 | B2 | 6/2008 | Truckai et al. |
| 8,663,220 | B2 | 3/2014 | Wiener et al. |
| 8,820,605 | B2 | 9/2014 | Shelton, IV |
| 9,125,662 | B2 | 9/2015 | Shelton, IV |
| 9,314,308 | B2 | 4/2016 | Parihar et al. |
| 9,949,785 | B2 | 4/2018 | Price et al. |
| 10,624,709 | B2 | 4/2020 | Remm |
| 10,835,307 | B2 | 11/2020 | Shelton, IV et al. |
| 11,229,471 | B2 | 1/2022 | Shelton, IV et al. |

(Continued)

OTHER PUBLICATIONS

International Search Report and Written Opinion dated Sep. 21, 2023, for International Application No. PCT/IB2023/056613, 18 pages.

*Primary Examiner* — Carl H Layno
*Assistant Examiner* — Aya Ziad Bakkar
(74) *Attorney, Agent, or Firm* — FBT Gibbons LLP

(57) ABSTRACT

A robotic surgical system including a controller, a surgical instrument, and a tool. The surgical instrument is configured to interact with a patient. The surgical instrument is operatively coupled with the controller. The tool is operatively coupled with the robotic surgical system. The tool includes a disassembly feature. The disassembly feature of the tool is configured to disconnect at least a portion of the surgical instrument from the robotic surgical system in response to instructions from the controller.

20 Claims, 14 Drawing Sheets

(56)　　　　　　References Cited

U.S. PATENT DOCUMENTS

| | | | |
|---|---|---|---|
| 11,690,642 B2 | 7/2023 | Black et al. | |
| 2006/0079874 A1 | 4/2006 | Faller et al. | |
| 2007/0191713 A1 | 8/2007 | Eichmann et al. | |
| 2008/0200940 A1 | 8/2008 | Eichmann et al. | |
| 2012/0292367 A1 | 11/2012 | Morgan et al. | |
| 2017/0238928 A1* | 8/2017 | Morgan | A61B 50/36 |
| 2018/0049824 A1 | 2/2018 | Harris et al. | |
| 2018/0168757 A1 | 6/2018 | Bono et al. | |
| 2019/0201046 A1 | 7/2019 | Shelton, IV et al. | |
| 2019/0201077 A1 | 7/2019 | Yates et al. | |
| 2019/0201080 A1 | 7/2019 | Messerly et al. | |
| 2019/0201091 A1 | 7/2019 | Yates et al. | |
| 2019/0201132 A1* | 7/2019 | Ugochuku | A61B 34/30 |
| 2019/0207857 A1 | 7/2019 | Shelton, IV et al. | |
| 2019/0274717 A1 | 9/2019 | Nott et al. | |
| 2020/0367977 A1 | 11/2020 | Liu et al. | |
| 2020/0405417 A1 | 12/2020 | Shelton, IV et al. | |
| 2022/0022982 A1* | 1/2022 | Hares | A61B 34/32 |
| 2022/0079692 A1* | 3/2022 | Staunton | A61B 34/76 |

\* cited by examiner

102

135 — MONITOR

106

138 — IMAGING MODULE

140 — GENERATOR MODULE

142 — MONOPOLAR

144 — BIPOLAR

146 — ULTRASONIC

126 — SMOKE EVACUATION MODULE

128 — SUCTION/IRRIGATION MODULE

130 — COMMUNICATION MODULE

132 — PROCESSOR MODULE

134 — STORAGE ARRAY

133 — OPERATING ROOM MAPPING MODULE

136

VISUALIZATION SYSTEM 108

ROBOTIC SYSTEM 110

INTELLIGENT INSTRUMENT 112

147

148

146

145

154

139

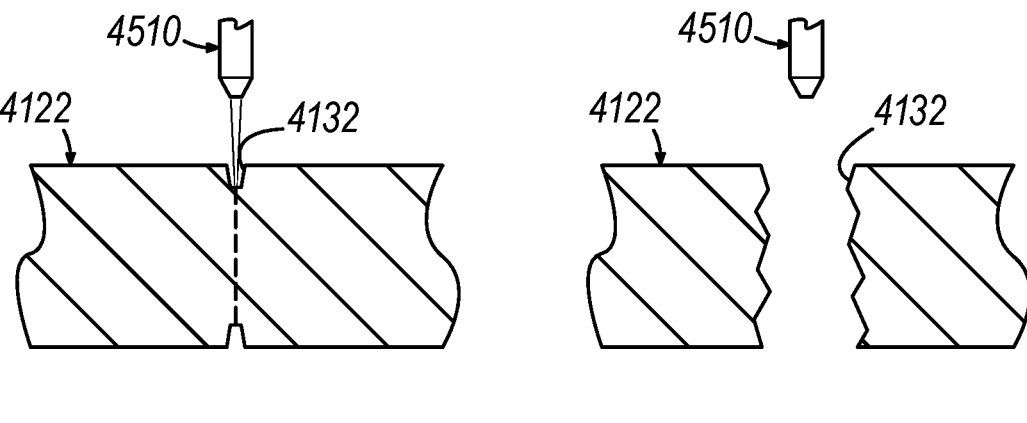
FIG. 14A                    FIG. 14B
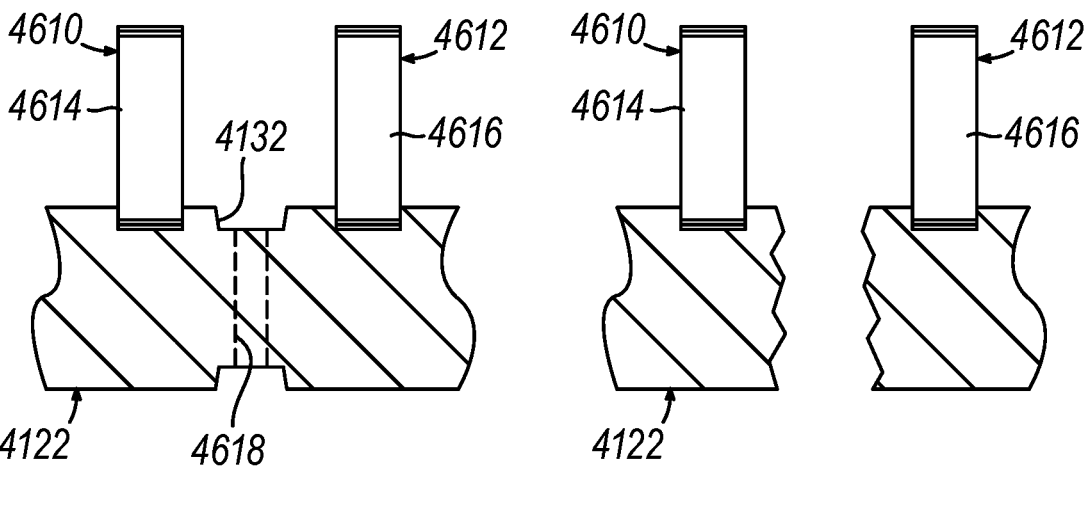
FIG. 15A                    FIG. 15B

1

ROBOTIC SURGICAL SYSTEM WITH REMOVABLE PORTION AND METHOD OF DISASSEMBLING SAME

BACKGROUND

A variety of ultrasonic surgical instruments include an end effector having a blade element that vibrates at ultrasonic frequencies to cut and/or seal tissue (e.g., by denaturing proteins in tissue cells). These instruments include one or more piezoelectric elements that convert electrical power into ultrasonic vibrations, which are communicated along an acoustic waveguide to the blade element. Examples of ultrasonic surgical instruments and related concepts are disclosed in U.S. Pub. No. 2006/0079874, entitled "Tissue Pad for Use with an Ultrasonic Surgical Instrument," published Apr. 13, 2006, now abandoned, the disclosure of which is incorporated by reference herein, in its entirety; U.S. Pub. No. 2007/0191713, entitled "Ultrasonic Device for Cutting and Coagulating," published Aug. 16, 2007, now abandoned, the disclosure of which is incorporated by reference herein, in its entirety; and U.S. Pub. No. 2008/0200940, entitled "Ultrasonic Device for Cutting and Coagulating," published Aug. 21, 2008, now abandoned, the disclosure of which is incorporated by reference herein, in its entirety.

Some instruments are operable to seal tissue by applying radiofrequency (RF) electrosurgical energy to the tissue. Examples of such devices and related concepts are disclosed in U.S. Pat. No. 7,354,440, entitled "Electrosurgical Instrument and Method of Use," issued Apr. 8, 2008, the disclosure of which is incorporated by reference herein, in its entirety; U.S. Pat. No. 7,381,209, entitled "Electrosurgical Instrument," issued Jun. 3, 2008, the disclosure of which is incorporated by reference herein, in its entirety.

Some instruments are capable of applying both ultrasonic energy and RF electrosurgical energy to tissue. Examples of such instruments are described in U.S. Pat. No. 9,949,785, entitled "Ultrasonic Surgical Instrument with Electrosurgical Feature," issued Apr. 24, 2018, the disclosure of which is incorporated by reference herein, in its entirety; U.S. Pat. No. 8,663,220, entitled "Ultrasonic Electrosurgical Instruments," issued Mar. 4, 2014, the disclosure of which is incorporated by reference herein, in its entirety; U.S. Pat. No. 10,835,307, entitled "Modular Battery Powered Handheld Surgical Instrument Containing Elongated Multi-Layered Shaft," issued Nov. 17, 2020, the disclosure of which is incorporated by reference herein, in its entirety; and U.S. Pat. No. 11,229,471, entitled "Modular Battery Powered Handheld Surgical Instrument with Selective Application of Energy Based on Tissue Characterization," issued Jan. 25, 2022, the disclosure of which is incorporated by reference herein, in its entirety.

In some scenarios, it may be preferable to have surgical instruments grasped and manipulated directly by the hand or hands of one or more human operators. In addition, or as an alternative, it may be preferable to have surgical instruments controlled via a robotic surgical system. Examples of robotic surgical systems and associated instrumentation are disclosed in U.S. Pat. No. 10,624,709, entitled "Robotic Surgical Tool with Manual Release Lever," published on May 2, 2019, the disclosure of which is incorporated by reference herein, in its entirety; U.S. Pat. No. 9,314,308, entitled "Robotic Ultrasonic Surgical Device With Articulating End Effector," issued on Apr. 19, 2016, the disclosure of which is incorporated by reference herein, in its entirety; U.S. Pat. No. 9,125,662, entitled "Multi-Axis Articulating and Rotating Surgical Tools," issued Sep. 8, 2015, the disclosure of which is incorporated by reference herein, in its entirety; U.S. Pat. No. 8,820,605, entitled "Robotically-Controlled Surgical Instruments," issued Sep. 2, 2014, the disclosure of which is incorporated by reference herein, in its entirety; U.S. Pub. No. 2019/0201077, entitled "Interruption of Energy Due to Inadvertent Capacitive Coupling," published Jul. 4, 2019, issued as U.S. Pat. No. 11,291,495 on Apr. 5, 2022, the disclosure of which is incorporated by reference herein, in its entirety; U.S. Pub. No. 2012/0292367, entitled "Robotically-Controlled End Effector," published on Nov. 11, 2012, now abandoned, the disclosure of which is incorporated by reference herein, in its entirety; and U.S. patent application Ser. No. 16/556,661, entitled "Ultrasonic Surgical Instrument with a Multi-Planar Articulating Shaft Assembly," filed on Aug. 30, 2019, issued as U.S. Pat. No. 11,690,642 on Jul. 4, 2023, the disclosure of which is incorporated by reference herein, in its entirety.

Such instruments and robotic surgical systems may be further be incorporated into a surgical system for performing procedures in a surgical environment, such as surgical operating theaters or rooms in a healthcare facility. A sterile field is typically created around the patient and may include properly attired, scrubbed healthcare professions as well as desired furniture and/or fixtures. Examples of such surgical systems and associated features are disclosed in U.S. Pat. Pub. No. 2019/0201046, entitled "Method for Controlling Smart Energy Devices," published on Jul. 4, 2019, issued as U.S. Pat. No. 11,589,888 on Feb. 28, 2023, the disclosure of which is incorporated by reference herein, in its entirety; U.S. Pat. Pub. No. 2019/0201080, entitled "Ultrasonic Energy Device Which Varies Pressure Applied by Clamp Arm to Provide Threshold Control Pressure at a Cut Progression Location," published on Jul. 4, 2019, issued as U.S. Pat. No. 11,419,667 on Aug. 23, 2022, the disclosure of which is incorporated by reference herein, in its entirety; U.S. Pat. Pub. No. 2019/0201091, entitled "Radio Frequency Energy Device for Delivering Combined Electrical Signals," published Jul. 4, 2019, issued as U.S. Pat. No. 11,364,075 on Jun. 21, 2022, the disclosure of which is incorporated by reference herein, in its entirety; U.S. Pat. Pub. No. 2019/0274717, entitled "Methods for Controlling Temperature in Ultrasonic Device," published Sep. 12, 2019, issued as U.S. Pat. No. 11,259,830 on Mar. 1, 2022, the disclosure of which is incorporated by reference herein, in its entirety; and U.S. Pat. Pub. No. 2019/0207857, entitled "Surgical Network Determination of Prioritization of Communication, Interaction, or Processing Based on System or Device Needs," published Jul. 4, 2019, issued as U.S. Pat. No. 10,892,995 on Jan. 21, 2021, the disclosure of which is incorporated by reference herein, in its entirety.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 14A depicts a schematic sectional view of a portion of the housing of FIG. 7 as a fifth exemplary disassembly feature is activated;

FIG. 14B depicts the schematic sectional view of the portion of the housing similar to FIG. 14A, but after separation using the disassembly feature of FIG. 14A;

FIG. 15A depicts a schematic sectional view of a sixth exemplary disassembly features moving from the first configuration toward the second configuration to separate a frangible portion of the surgical instrument of FIG. 7;

FIG. 15B depicts the schematic sectional view of the disassembly features of FIG. 15A, but with the frangible portion in a separated state;

Figure 1:
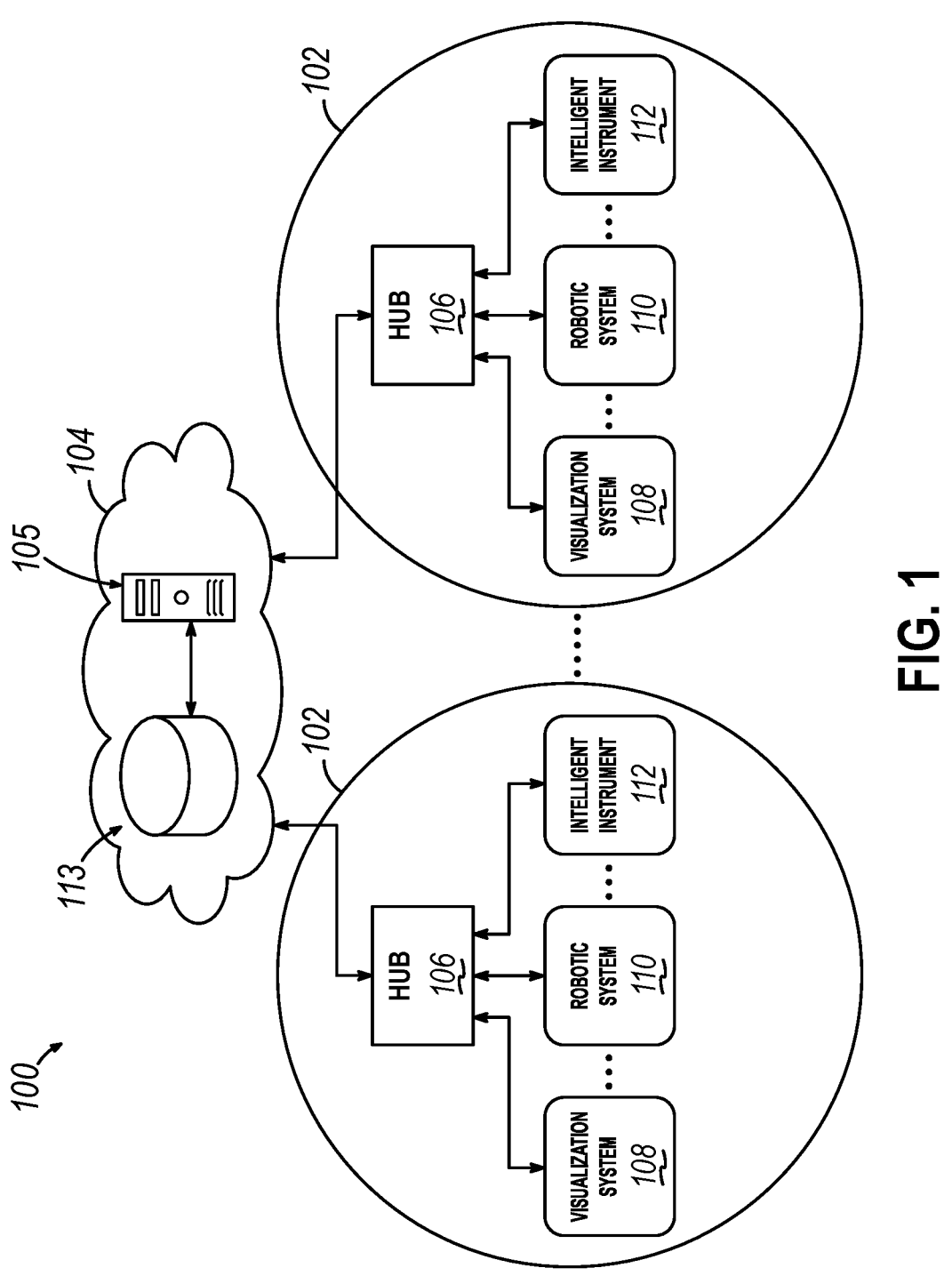
FIG. 1 depicts a block diagram of an example a computer-implemented interactive surgical system.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. In addition, the terms "upper," "lower," "top," "bottom," "above," and "below," are used with respect to the examples and associated figures and are not intended to unnecessarily limit the invention described herein.

I. EXAMPLE OF A SURGICAL SYSTEM

With respect to FIG. 1, a computer-implemented interactive surgical system (100) includes one or more surgical systems (102) and a cloud-based system (e.g., a cloud (104) that may include a remote server (113) coupled to a storage device (105)). Each surgical system (102) of the present example includes at least one surgical hub (106) in communication with cloud (104) that may include a remote server (113). In one example, as illustrated in FIG. 1, surgical system (102) includes a visualization system (108), a robotic system (110), and a handheld intelligent surgical instrument (112), which are configured to communicate with one another and/or hub (106). In some aspects, a surgical system (102) may include an M number of hubs (106), an N number of visualization systems (108), an O number of robotic systems (110), and a P number of handheld intelligent surgical instruments (112), where M, N, O, and P are integers greater than or equal to one. In any case, any suitable combination of features provided below may be incorporated into an exemplary surgical system, such as surgical system (100), and used in the surgical theater in order to perform a desired surgical procedure as would be apparent to one skilled in the art in view of the teachings herein.

Figure 2:
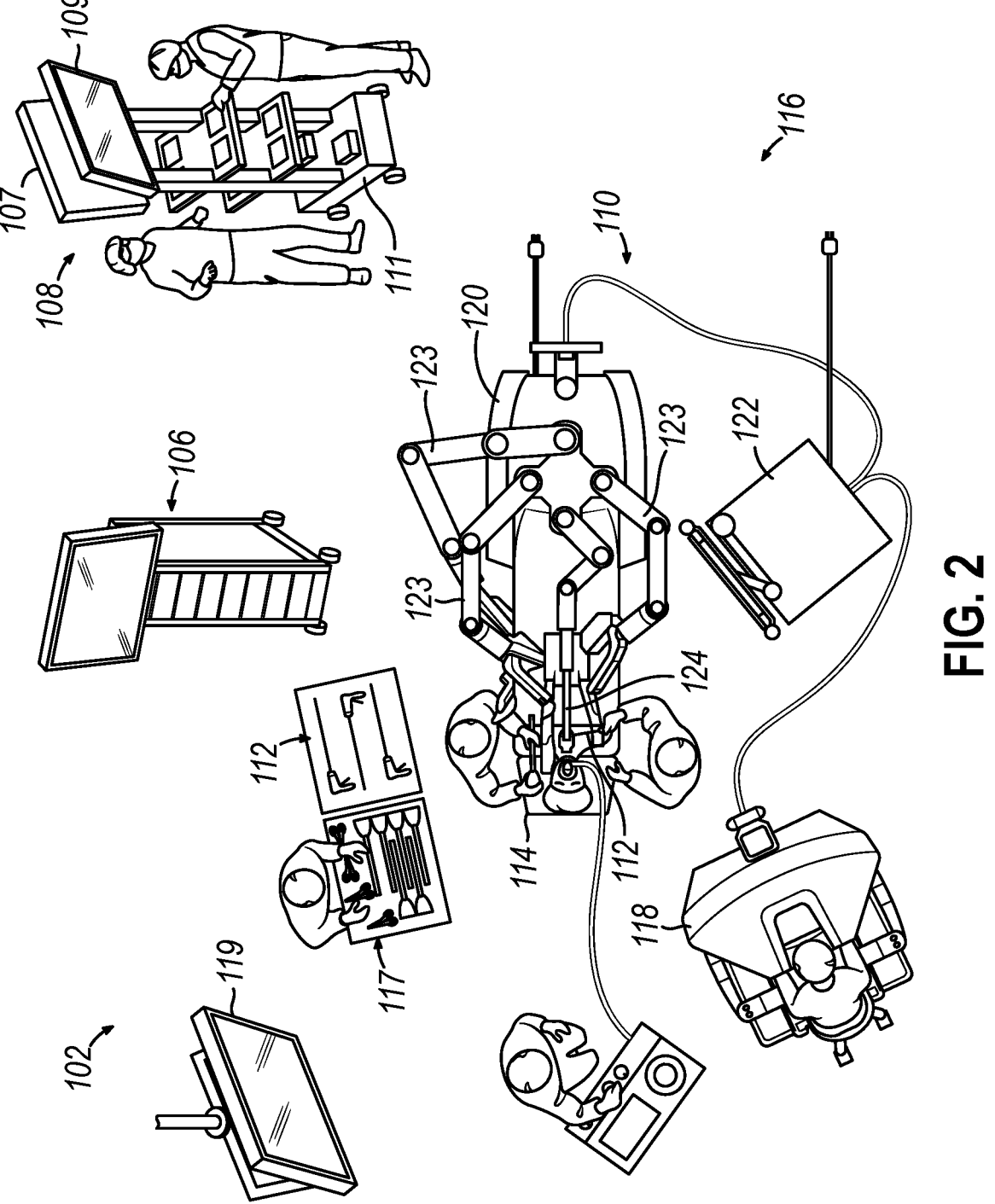
FIG. 2 depicts a top schematic view of an example of a surgical system for performing a surgical procedure in an operating room of a healthcare facility.

FIG. 2 depicts an example of a surgical system (102) being used to perform a surgical procedure on a patient who is lying down on an operating table (114) in a surgical operating room (116). A robotic system (110) is used in the surgical procedure as a part of surgical system (102). Robotic system (110) includes a surgeon's console (118), a patient side cart (120) (surgical robot), and a surgical robotic hub (122). Patient side cart (120) can manipulate at least one removably coupled surgical tool (117) with any one of a plurality of surgical arms (123) through a minimally invasive incision in the body of the patient while the surgeon views the surgical site through console (118). An image of the surgical site can be obtained by a medical imaging device (124), which can be manipulated by patient side cart (120) to orient imaging device (124). Robotic hub (122) can be used to process the images of the surgical site for subsequent display to the surgeon through console (118).

Other types of robotic systems can be readily adapted for use with surgical system (102). Various examples of robotic systems and surgical tools that are suitable for use with the present disclosure are described in U.S. Provisional Patent Application Ser. No. 62/611,339, entitled "Robot Assisted Surgical Platform," filed Dec. 28, 2017, the disclosure of which is herein incorporated by reference in its entirety.

Various examples of cloud-based analytics that are performed by cloud (104, and are suitable for use with the present disclosure, are described in U.S. Provisional Patent Application Ser. No. 62/611,340, entitled Cloud-Based Medical Analytics," filed Dec. 28, 2017, the disclosure of which is herein incorporated by reference in its entirety.

In various aspects, imaging device (124) includes at least one image sensor and one or more optical components. Suitable image sensors include, but are not limited to, Charge-Coupled Device (CCD) sensors and Complementary Metal-Oxide Semiconductor (CMOS) sensors. In various aspects, imaging device (124) is configured for use in a minimally invasive procedure. Examples of imaging devices suitable for use with the present disclosure include, but not limited to, an arthroscope, angioscope, bronchoscope, choledochoscope, colonoscope, cytoscope, duodenoscope, enteroscope, esophagogastro-duodenoscope (gastroscope), endoscope, laryngoscope, nasopharyngo-neproscope, sigmoidoscope, thoracoscope, and ureteroscope. Some aspects of spectral and multi-spectral imaging are described in greater detail under the heading "Advanced Imaging Acquisition Module" in U.S. Provisional Patent Application Ser. No. 62/611,341, entitled "Interactive Surgical Platform," filed Dec. 28, 2017, the disclosure of which is herein incorporated by reference in its entirety.

Strict sterilization of the operating room and surgical equipment is required during any surgery. The strict hygiene and sterilization conditions required in a "surgical theater,"

i.e., an operating or treatment room, necessitate the highest possible sterility of all medical devices and equipment. Part of that sterilization process is the need to sterilize anything that comes in contact with the patient or penetrates the sterile field. It will be appreciated that the sterile field may be considered a specified area, such as within a tray or on a sterile towel, that is considered free of microorganisms, or the sterile field may be considered an area, immediately around a patient, who has been prepared for a surgical procedure. The sterile field may include the scrubbed team members, who are properly attired, and all furniture and fixtures in the area.

In addition to the introduction of any features of surgical system (100), furniture, or fixtures into the sterile field requiring sterilization, additional complications may result from removal of these features from the sterile field, particularly when such features may have contacted, or presumed to have contacted, the patient, including any tissues and/or fluids associated with the surgical procedure. Such contamination of these features from the patient often requires special consideration during or after the surgical procedure, particularly when processing these features for disposal, reuse, or remanufacturing as desired. In one example, surgical system (100) and/or healthcare professionals associated with the surgical procedure may be specifically equipped to address such processing as discussed below in greater detail.

As illustrated in FIG. 2, a primary display (119) is positioned in the sterile field to be visible to an operator at operating table (114). In addition, a visualization tower (111) is positioned outside the sterile field. Visualization tower (111) includes a first non-sterile display (107) and a second non-sterile display (109), which face away from each other. Visualization system (108), guided by hub (106), is configured to utilize displays (107, 109, 119) to coordinate information flow to operators inside and outside the sterile field. For example, hub (106) may cause visualization system (108) to display a snapshot of a surgical site, as recorded by imaging device (124), on a non-sterile display (107) or (109), while maintaining a live feed of the surgical site on the primary display (119). The snapshot on non-sterile display (107) or display (109) can permit a non-sterile operator to perform a diagnostic step relevant to the surgical procedure, for example.

In one aspect, hub (106) is also configured to route a diagnostic input or feedback entered by a non-sterile operator at visualization tower (111) to primary display (119) within the sterile field, where it can be viewed by a sterile operator at the operating table. In one example, the input can be in the form of a modification to the snapshot displayed on non-sterile display (107) or display (109), which can be routed to primary display (119) by hub (106).

Referring to FIG. 2, a surgical instrument (112) is being used in the surgical procedure as part of surgical system (102). Hub (106) is also configured to coordinate information flow to a display of the surgical instrument (112) such as in, for example, U.S. Provisional Patent Application Ser. No. 62/611,341, entitled "Interactive Surgical Platform," filed Dec. 28, 2017, the disclosure of which is herein incorporated by reference in its entirety. A diagnostic input or feedback entered by a non-sterile operator at visualization tower (111) can be routed by hub (106) to surgical instrument display (115) within the sterile field, where it can be viewed by the operator of surgical instrument (112). Example surgical instruments that are suitable for use with surgical system (102) are described under the heading "Surgical Instrument Hardware" and in U.S. Provisional Patent Application Ser. No. 62/611,341, entitled "Interactive Surgical Platform," filed Dec. 28, 2017, the disclosure of which is herein incorporated by reference in its entirety, for example.

Figure 3:
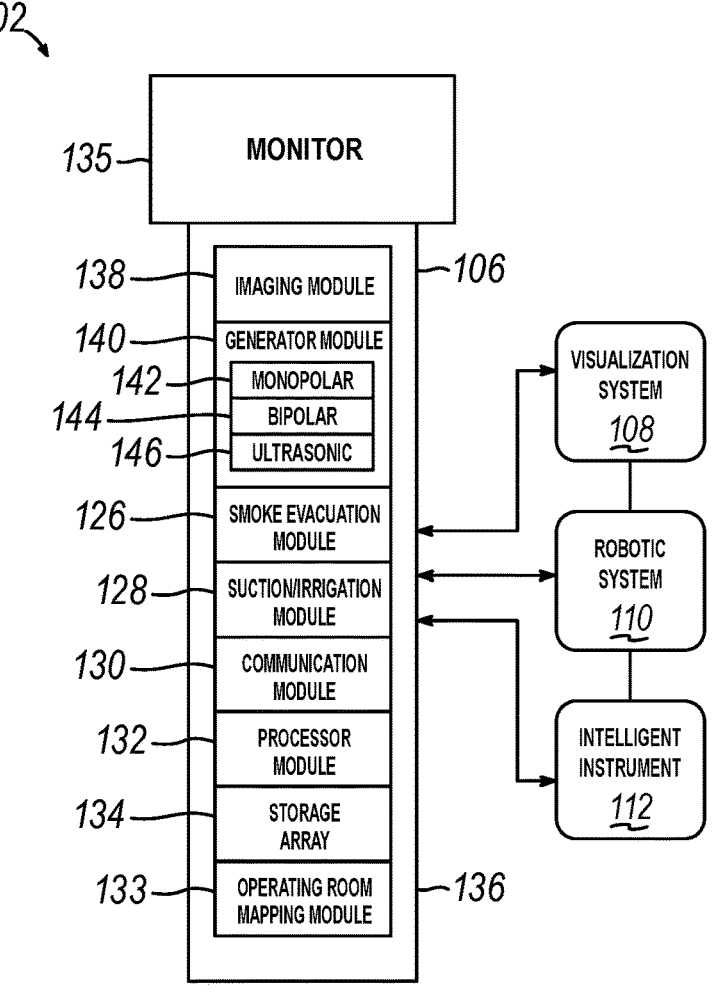
FIG. 3 depicts a side schematic view of an example of a surgical hub of the surgical system of FIG. 2.

Referring now to FIG. 3, a hub (106) is depicted in communication with a visualization system (108), a robotic system (110), and a handheld intelligent surgical instrument (112). Hub (106) includes a hub display (135), an imaging module (138), a generator module (140), a communication module (130), a processor module (132), and a storage array (134). In certain aspects, as illustrated in FIG. 3, hub (106) further includes a smoke evacuation module (126), a suction/irrigation module (128), and/or an operating room mapping module (133).

During a surgical procedure, energy application to tissue, for sealing and/or cutting, is generally associated with smoke evacuation, suction of excess fluid, and/or irrigation of the tissue. Fluid, power, and/or data lines from different sources are often entangled during the surgical procedure. Valuable time can be lost addressing this issue during a surgical procedure. Detangling the lines may necessitate disconnecting the lines from their respective modules, which may require resetting the modules. The hub modular enclosure (136) offers a unified environment for managing the power, data, and fluid lines, which reduces the frequency of entanglement between such lines.

Figure 4:
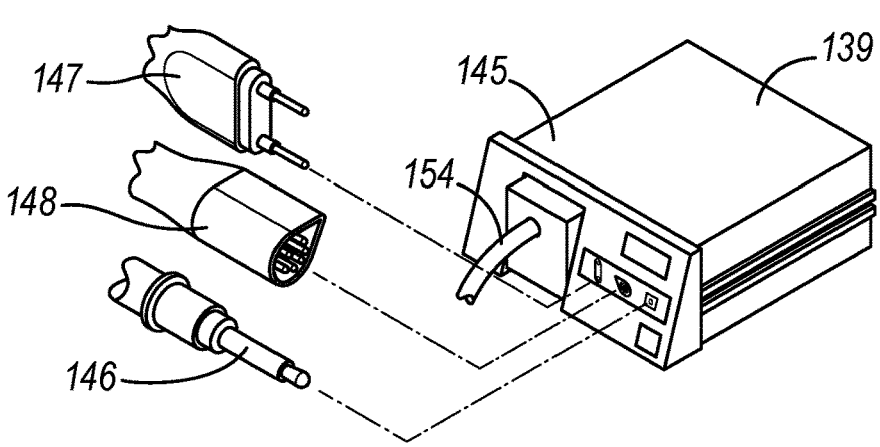
FIG. 4 depicts a perspective view of a combination generator module with bipolar, ultrasonic, and monopolar contacts of the surgical system of FIG. 2.

Referring to FIGS. 3-4, aspects of the present disclosure are presented for a hub modular enclosure (136) that allows the modular integration of a generator module (140), a smoke evacuation module (126), and a suction/irrigation module (128). Hub modular enclosure (136) further facilitates interactive communication between modules (140, 126, 128). As shown in FIG. 4, generator module (140) can be a generator module with integrated monopolar, bipolar, and ultrasonic components supported in a single housing unit (139) slidably insertable into hub modular enclosure (136). As illustrated in FIG. 4, generator module (140) can be configured to connect to a monopolar device (146), a bipolar device (147), and an ultrasonic device (148). Alternatively, generator module (140) may comprise a series of monopolar, bipolar, and/or ultrasonic generator modules that interact through hub modular enclosure (136). Hub modular enclosure (136) can be configured to facilitate the insertion of multiple generators and interactive communication between the generators docked into the hub modular enclosure (136) so that the generators would act as a single generator.

Figure 5:
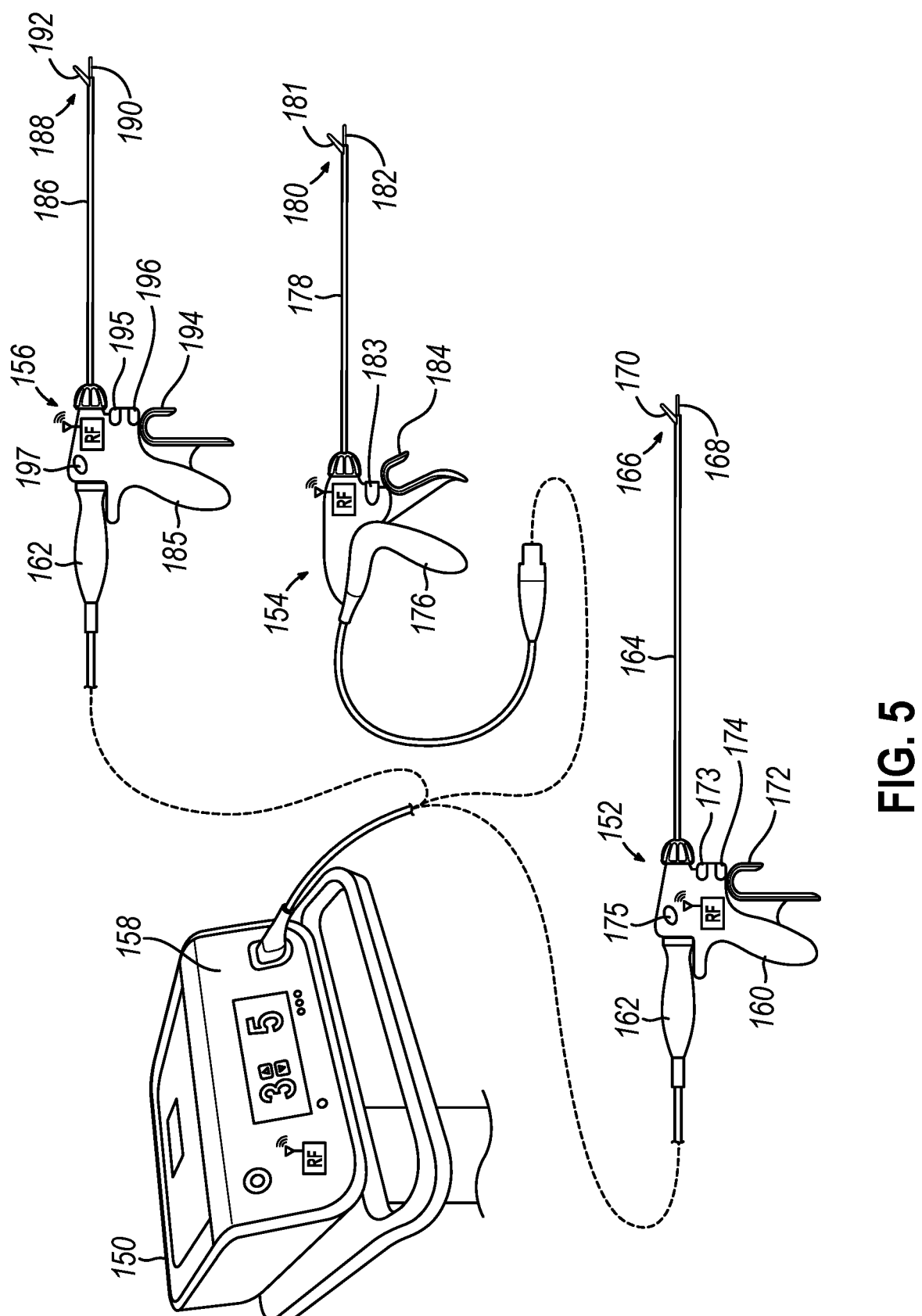
FIG. 5 depicts a side schematic view of an exemplary generator and various examples of surgical instruments for use with the surgical system of FIG. 2.

FIG. 5 illustrates one form of a generator (150) and various surgical instruments (152, 154, 156) usable therewith, where surgical instrument (152) is an ultrasonic surgical instrument (152), surgical instrument (154) is an RF electrosurgical instrument (154), and multifunction surgical instrument (156) is a combination ultrasonic/RF electrosurgical instrument (156). Generator (150) is configurable for use with a variety of surgical instruments. According to various forms, generator (150) may be configurable for use with different surgical instruments of different types including, for example, ultrasonic surgical instruments (152), RF electrosurgical instruments (154), and multifunction surgical instruments (156) that integrate RF and ultrasonic energies delivered simultaneously from generator (150). Although generator (150) of the present example in FIG. 5 is shown separate from surgical instruments (152, 154, 156), generator (150) may alternatively be formed integrally with any of surgical instruments (152, 154, 156) to form a unitary surgical system. Generator (150) comprises an input device (158) located on a front panel of generator (150) console.

Input device (158) may comprise any suitable device that generates signals suitable for programming the operation of generator (150). Generator (150) may be configured for wired or wireless communication.

Generator (150) of the present example is configured to drive multiple surgical instruments (152, 154, 156). One example of such surgical instrument is ultrasonic surgical instrument (152) and comprises a handpiece (160), an ultrasonic transducer 162, a shaft assembly (164), and an end effector (166). End effector (166) includes an ultrasonic blade (168) acoustically coupled to ultrasonic transducer (162) and a clamp arm (170). Handpiece (160) has a trigger (172) to operate clamp arm (170) and a combination of toggle buttons (173, 174, 175) to energize and drive ultrasonic blade (168) or other function. Toggle buttons (173, 174, 175) can be configured to energize ultrasonic transducer (162) with generator (150).

Generator (150) also is configured to drive another example of surgical instrument (154). RF electrosurgical instrument (154) includes a handpiece (176), a shaft assembly (178), and an end effector (180). End effector (180) includes electrodes in clamp arms (181, 182) and return through an electrical conductor portion of shaft assembly (178). Electrodes are coupled to and energized by a bipolar energy source within generator (150). Handpiece (176) includes a trigger (183) to operate clamp arms (181, 182) and an energy button (184) to actuate an energy switch to energize electrodes in end effector (180).

Generator (150) also is configured to drive multifunction surgical instrument (156). Multifunction surgical instrument (156) includes a handpiece (185), a shaft assembly (186), and an end effector (188). End effector (188) has an ultrasonic blade (190) and a clamp arm (192). Ultrasonic blade (190) is acoustically coupled to ultrasonic transducer (162). Handpiece (185) has a trigger (194) to operate clamp arm (192) and a combination of toggle buttons (195, 196, 197) to energize and drive ultrasonic blade (190) or other function. Toggle buttons (195, 196, 197) can be configured to energize ultrasonic transducer (162) with generator (150) and energize ultrasonic blade (190) with a bipolar energy source also contained within generator (150). It will be appreciated that handpieces (160, 176, 185) may be replaced with a robotically controlled instrument for incorporating one or more aspects of surgical instruments (152, 154, 156). Accordingly, the term "handpiece" should not be limited to this context and to handheld use.

As used throughout this description, the term "wireless" and its derivatives may be used to describe circuits, devices, systems, methods, techniques, communications channels, etc., that may communicate data through the use of modulated electromagnetic radiation through a non-solid medium. The term does not imply that the associated devices do not contain any wires, although in some aspects they might not. The communication module may implement any of a number of wireless or wired communication standards or protocols, including but not limited to Wi-Fi (IEEE 802.11 family), WMAX (IEEE 802.16 family), IEEE 802.20, long term evolution (LTE), Ev-DO, HSPA+, HSDPA+, HSUPA+, EDGE, GSM, GPRS, CDMA, TDMA, DECT, Bluetooth, Ethernet derivatives thereof, as well as any other wireless and wired protocols that are designated as 3G, 4G, 5G, and beyond. The computing module may include a plurality of communication modules. For instance, a first communication module may be dedicated to shorter range wireless communications such as Wi-Fi and Bluetooth and a second communication module may be dedicated to longer range wireless communications such as GPS, EDGE, GPRS, CDMA, WiMAX, LTE, Ev-DO, and others.

As used herein a processor or processing unit is an electronic circuit which performs operations on some external data source, usually memory or some other data stream. The term is used herein to refer to the central processor (central processing unit) in a system or computer systems (especially systems on a chip (SoCs)) that combine a number of specialized "processors."

As used herein, a system on a chip or system on chip (SoC or SOC) is an integrated circuit (also known as an "IC" or "chip") that integrates all components of a computer or other electronic systems. It may contain digital, analog, mixed-signal, and often radiofrequency functions, all on a single substrate. A SoC integrates a microcontroller (or microprocessor) with advanced peripherals like graphics processing unit (GPU), Wi-Fi module, or coprocessor. A SoC may or may not contain built-in memory.

As used herein, a microcontroller or controller is a system that integrates a microprocessor with peripheral circuits and memory. A microcontroller (or MCU for microcontroller unit) may be implemented as a small computer on a single integrated circuit. It may be similar to a SoC; an SoC may include a microcontroller as one of its components. A microcontroller may contain one or more core processing units (CPUs) along with memory and programmable input/output peripherals. Program memory in the form of Ferroelectric RAM, NOR flash or OTP ROM is also often included on chip, as well as a small amount of RAM. Microcontrollers may be employed for embedded applications, in contrast to the microprocessors used in personal computers or other general purpose applications consisting of various discrete chips.

As used herein, the term controller or microcontroller may be a stand-alone IC or chip device that interfaces with a peripheral device. This may be a link between two parts of a computer or a controller on an external device that manages the operation of (and connection with) that device. Modular devices include the modules (as described in connection with FIG. 3, for example) that are receivable within a surgical hub and the surgical devices or instruments that can be connected to the various modules in order to connect or pair with the corresponding surgical hub. The modular devices include, for example, intelligent surgical instruments, medical imaging devices, suction/irrigation devices, smoke evacuators, energy generators, ventilators, insufflators, and displays. The modular devices described herein can be controlled by control algorithms. The control algorithms can be executed on the modular device itself, on the surgical hub to which the particular modular device is paired, or on both the modular device and the surgical hub (e.g., via a distributed computing architecture). In some exemplifications, the modular devices' control algorithms control the devices based on data sensed by the modular device itself (i.e., by sensors in, on, or connected to the modular device). This data can be related to the patient being operated on (e.g., tissue properties or insufflation pressure) or the modular device itself (e.g., the rate at which a knife is being advanced, motor current, or energy levels). For example, a control algorithm for a surgical stapling and cutting instrument can control the rate at which the instrument's motor drives its knife through tissue according to resistance encountered by the knife as it advances.

II. ROBOTIC SURGICAL SYSTEM WITH REMOVABLE PORTION

In some instances, it may be desirable to provide a surgical instrument that includes components capable of delivering ultrasonic energy, RF energy, or both ultrasonic and RF energy that easily open to provide access to the internal components for separation into separate waste streams with minimal tools. Surgery customarily takes place within the sterile field, as described above. The sterile field, being free of microorganisms, enables the surgical team to decrease the chance of infection by ensuring that only sterilized equipment and tools are used within the sterile field. Surgical instruments are sterilized and packaged within sterile containers that are passed into the sterile field. Health care professionals may be required to disassemble the surgical instruments within the sterile field after a surgical procedure by hand or with tools provided within the sterile containers. For example, a torque wrench provided for assembling a surgical instrument, may have additional features to disassemble the surgical instrument.

The surgical instruments include additional features that facilitate disassembly and removal of internal components. These separate waste streams are predetermined based on the material of the component or the use of the component. For example, the waste streams may include recycling, disposal, or refurbishing. Components placed in the disposal waste stream would be disposed of in a land fill. Components placed in the recycling waste stream may be further separated, shredded, and melted down into a base component. Components placed in the refurbishing waste stream would be cleaned, tested, repaired, and refitted within another surgical instrument. For example, the plastic and metal components may be separated into one waste stream for disposal, heavy metals from an integrated circuit may be separated into a second waste stream for recycling, and ultrasonic transducers may be separated into a third waste stream for refurbishing.

A. Overview of Robotic Surgical System

Figure 6:
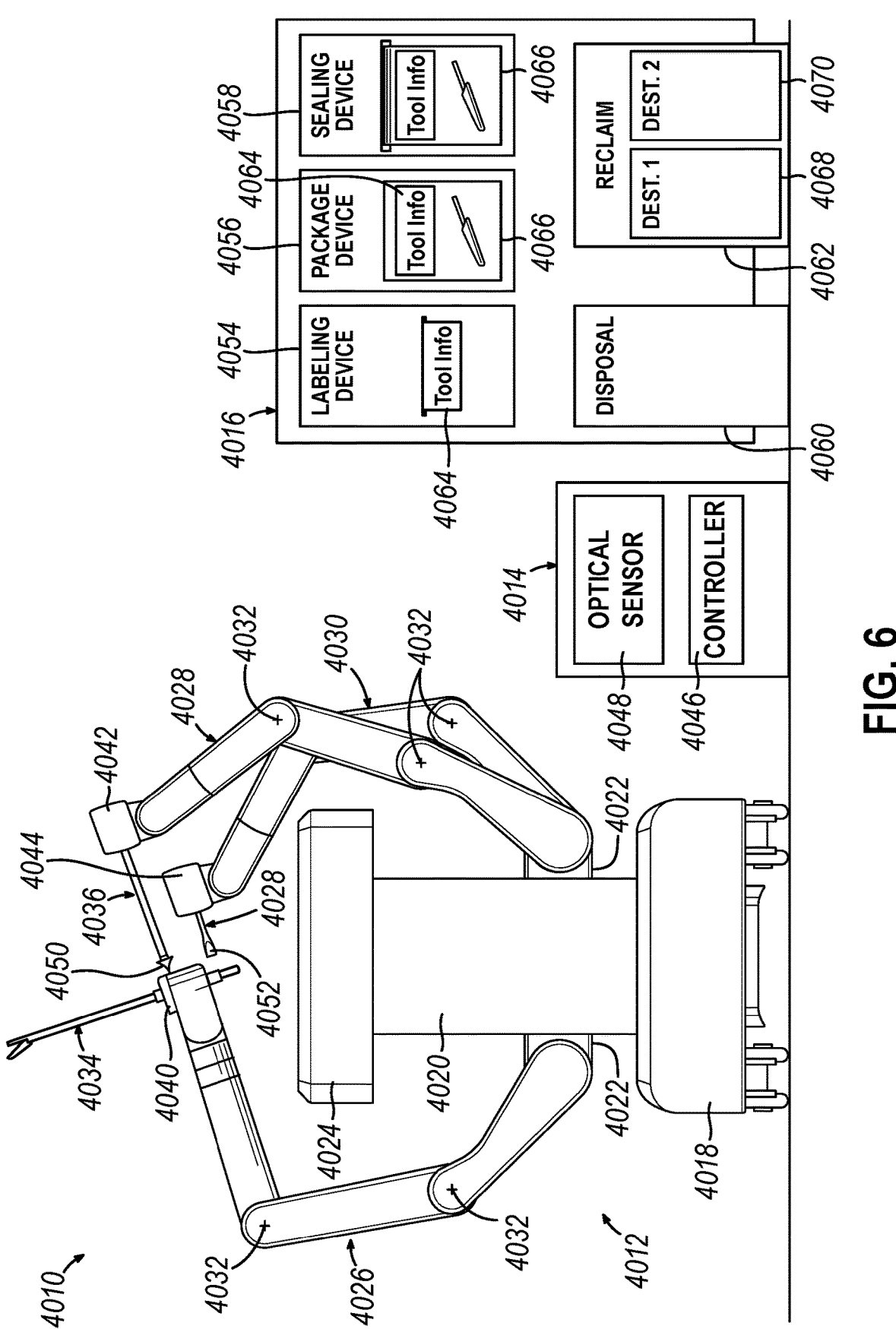
FIG. 6 depicts a schematic front view of an exemplary robotic surgical system that includes a plurality of tools.

FIG. 6 shows an exemplary robotic surgical system (4010) that includes a patient side cart (4012) (surgical robot), a surgical robotic hub (4014), and a packaging system (4016). Patient side cart (4012) may be similar to patient side cart (120), and surgical robotic hub (4014) may be similar to surgical robotic hub (122) (see FIG. 2), except where otherwise indicated below. While not shown, robotic surgical system (4010) may include additional features similar to robotic surgical system (110) (e.g., a surgeon's console etc.).

As shown in FIG. 6, patient side cart (4012) includes a base (4018), a column (4020), vertical carriages (4022), and an operating table (4024). Base (4018) and column (4020) collectively support operating table (4024). Vertical carriages (4022) are configured to move up or down along, or relative to, column (4020). Operating table (4024) is configured to support a patient thereon, and may be similar to operating table (114). Vertical carriages support plurality of robotic arms, which may be similar to surgical arms (123) that are shown in FIG. 2. While the plurality of robotic arms are shown as including first, second, and third robotic arms (4026, 4028, 4030), more robotic arms (e.g., fourth, fifth, sixth arms etc.) or fewer robotic arms (e.g., first and second arms) are also envisioned. First, second, and third robotic arms (4026, 4028, 4030) extend outwardly from column (4020). As shown, each of first, second, and third robotic arms (4026, 4028, 4030) include joints (4032) allowing for multiple degrees of freedom (e.g., seven or eight degrees of freedom). First robotic arm (4026) is operatively coupled with a surgical instrument (4034) at a first interface (4040). Surgical instrument (4034) is configured to interact with the patient. Surgical instrument (4034) may be similar to surgical instruments (112, 152, 154, 156) described above.

Robotic surgical system (4010) includes a plurality of tools. While FIG. 6 schematically shows the plurality of robotic tools as including tools (4036, 4038), more tools (e.g., third, fourth, fifth, sixth tools etc.) or fewer tools (e.g., first tool) are also envisioned. As schematically shown, second robotic arm (4028) is operatively coupled with tool (4036) at a second interface (4042), and third robotic arm (4030) is operatively coupled with tool (4038) at a third interface (4044).

With continued reference FIG. 6, hub (4014) includes a controller (4046) and an optional sensor (4048). Tools (4036, 4038) are operatively coupled with controller (4046). Disassembly feature (4050) of tool (4036) and/or disassembly feature (4052) of tool (4038) is configured to disconnect at least a portion of surgical instrument (4034) from robotic surgical system (4010) in response to instructions from controller (4046). Controller (4046) may autonomously instruct tool (4036) to disconnect at least a portion of surgical instrument (4034) from robotic surgical system (4010). As used herein, autonomously is intended to mean being capable of performing an operation without requiring additional user instruction once commenced. Controller (4046) is configured to instruct disassembly feature (4050) of tool (4036) to disconnect surgical instrument (4034) in response to feedback received from sensor (4048). In some versions, sensor (4048) may include an optical sensor configured to determine whether people are present in operating room (116).

With continued reference to FIG. 6, packaging system (4016) includes a labeling device (4054), a packaging device (4056) (e.g., a bagging device), a sealing device (4058), a disposal apparatus (4060), and a reclamation apparatus (4062). Labeling device (4054) is configured to dispense labels (4064). Labels (4064) may include tool information (e.g., serial numbers, manufacturing information, use information, etc.). Packaging device (4056) is configured to dispense a package (4066). Label (4064) may be affixed to an exterior surface of package (4066). In some versions, label (4064) may be already attached to package (4066). Package (4066) is configured to receive portion(s) of surgical instrument (4034) in response to instructions from controller (4046). Package (4066) may have a variety of shapes, sizes, and forms. For example, package (4066) may include flexible bags, rigid containers, and/or semi-rigid containers. Controller (4046) is configured to instruct tool (4036) and/or tool (4038) to insert portion of surgical instrument (4034) into package (4066). This may provide personnel within operating room (116) with bagging capability alongside patient side cart (4012).

Packaging system (4016) functions in coordination with patient side cart (4012) so that robotic arms (4026, 4028, 4030) may locate package (4066), allow package (4066) to be automatically dispensed, open package (4066), and close package (4066) when surgical instrument (4034) is located within an interior of package (4066). Sealing device (4058) may seal package (4066) after portion(s) of surgical instrument (4034) is received by package (4066) in response to instructions from controller (4046). Reclamation apparatus (4062) may include first and second shipping containers (4068, 4070). First shipping container (4068) may be used to ship package (4066) to a first location, and second shipping container (4070) may be used to ship package (4066) to a second location that is different from the first location.

At least one of tools (4036, 4038) includes a disassembly feature (4050, 4052). Robotic surgical system (4010) utilizes the interaction of at least surgical instrument (4034) and tools (4036) to achieve the desired disassembly. As will be described in greater detail below, tools (4036, 4038) may utilization discrete strokes or forces for disassembly. For example, tool (4036) may disassemble a first portion of surgical instrument (4034) and tool (4038) may disassemble a different second portion of surgical instrument (4034). Alternatively, disassembly features (4050, 4052) of tools (4036, 4038) may be used in combination (or even in combination with other tools (not shown)) to disassemble surgical instrument (4034). In some versions, disassembly features (4050, 4052) of tools (4036, 4038) may be used in combination simultaneously. In some versions, only tool (4036) includes a disassembly feature (4050), and tool (4038) includes a surgical instrument (e.g., surgical instruments (112, 152, 154, 156)). While not shown, in some versions, surgical instrument (4034) may be used to disassemble at least a portion of tools (4036, 4038).

B. Exemplary Surgical Instrument

Figure 7:
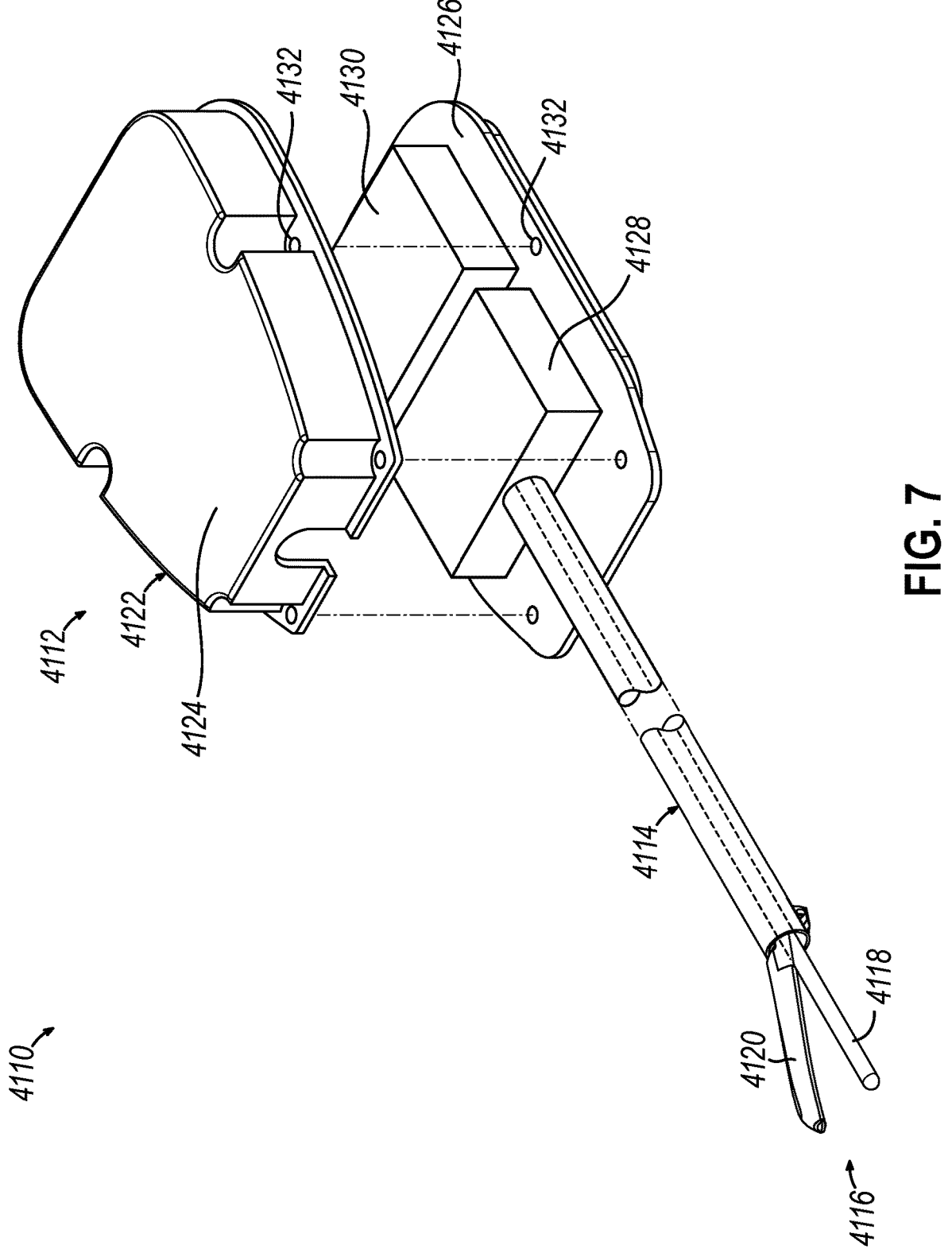
FIG. 7 depicts a perspective view of a surgical instrument, where a housing of the surgical instrument is partially removed to expose reclaimable components.

FIG. 7 shows a perspective view of an exemplary surgical instrument (4110) that may be used instead of surgical instrument (112, 152, 154, 156, 4034). Surgical instrument (4110) may be configured to deliver ultrasonic energy, Radio Frequency ("RF") energy, or both. While surgical instrument (4110) is configured to be operatively coupled with first robotic arm (4026) (see FIG. 6) at first interface (4040) (see FIG. 6), surgical instrument (4110) may alternatively be hand-held. Surgical instrument (4110) includes a body (4112), a shaft assembly (4114), and an end effector (4116). End effector (4116) includes an ultrasonic blade (4118) disposed on a first jaw and a clamp arm (4120) disposed on an opposing second jaw. Clamp arm (4120) is configured to pivot relative to ultrasonic blade (4118). Body (4112) includes a housing (4122) and a plurality of reclaimable components. Housing (4122) is shown as including first and second housing portions (4124, 4126), which may also be referred to as shroud portions. As shown and described below with reference to FIGS. 9-13B, first and second housing portions (4124, 4126) may be coupled using a variety of different coupling structures.

Referring back to FIG. 6 as well as FIG. 7, first housing portion (4124) is separated from second housing portion (4126). While the plurality of reclaimable components are shown as first and second reclaimable components (4128, 4130), more reclaimable components (e.g., third reclaimable component, fourth reclaimable component, etc.) or fewer reclaimable components are envisioned. Controller (4046) may autonomously instruct disassembly feature (4050) and/or disassembly feature (4052) to disconnect first and second reclaimable components (4128, 4130). In some versions, surgical instrument (4110) may be in the form of an ultrasonic surgical instrument that includes ultrasonic components. First reclaimable component (4124) includes an ultrasonic waveguide (which may include ultrasonic blade (4118)). Second reclaimable component (4130) includes an ultrasonic transducer. Controller (4046) may autonomously instruct disassembly feature (4050) and/or disassembly feature (4052) to disconnect the ultrasonic waveguide and the ultrasonic transducer from patient side cart (4012). With first and second housing portions (4124, 4126) released, second reclaimable component (4130) (e.g., the ultrasonic transducer) is exposed for subsequent removal. Surgical instrument (4110) includes markers (4132) to indicate to controller (4046) the predetermined disassembly location.

C. Exemplary Surgical Tool

Figure 8:
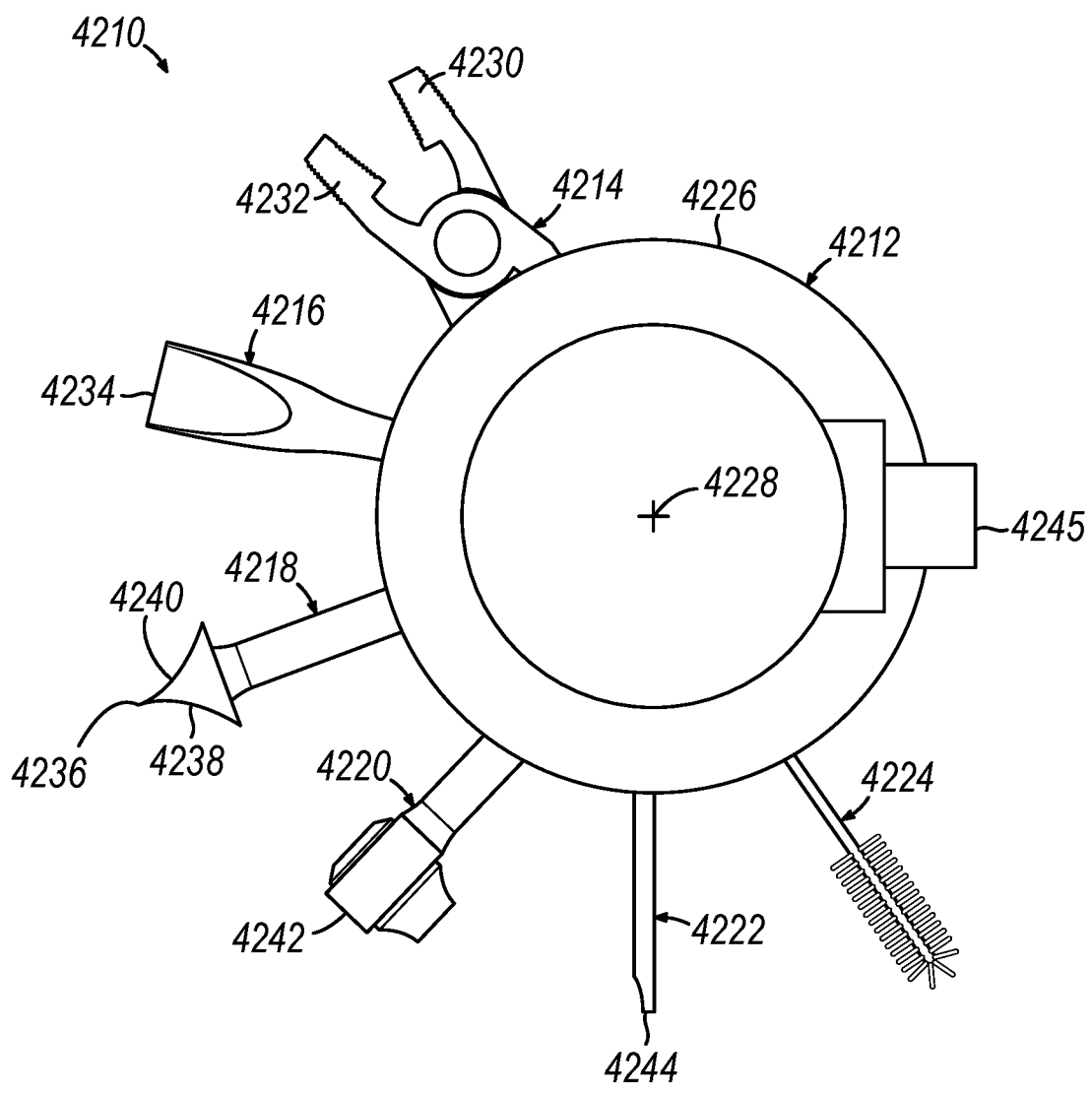
FIG. 8 depicts a top plan view of an exemplary tool that includes a plurality of disassembly features.

FIG. 8 shows a view of second exemplary tool (4210) that may be used place of tools (4036, 4038). Tool (4210) may be also referred to as a multitool. Tool (4210) includes a body (4212) and a plurality of disassembly features. Body (4212) may rotate about a center point (4228). While the plurality of disassembly features is shown as disassembly features (4214, 4216, 4218, 4220, 4222, 4224), more or fewer disassembly features are envisioned. Disassembly features (4214, 4216, 4218, 4220, 4222, 4224) are shown as extending outwardly from a periphery (4226) of body (4212). Disassembly features (4214, 4216, 4218, 4220, 4222, 4224) may have a variety of shapes and sizes. Disassembly features (4214, 4216, 4218, 4220, 4222, 4224) are configured to remove at least a portion of housing (4122) of surgical instrument (4110). In some versions, disassembly features (4214, 4216, 4218, 4220, 4222, 4224) may be removed, and different disassembly features (4214, 4216, 4218, 4220, 4222, 4224) inserted allowing for a variety of disassembly features depending on surgical instrument (4110) to be disassembled. Once controller (4046) receives the disassembly instructions (e.g., a device code), controller (4046) obtains desired disassembly features (4214, 4216, 4218, 4220, 4222, 4224), and then performs disassembly instructions based on that surgical instrument (4110).

Disassembly feature (4214) is shown as a pair of pliers, but may also function as a pair of reverse pliers. Disassembly feature (4214) includes opposing first and second jaws (4230, 4232) that are configured to move relative to each other as shown and described below with reference to FIGS. 9-10. Disassembly feature (4216) is shown as a scraper. While disassembly feature (4216) is shown as having a distal most end (4234) that is planar and blunt, distal most end (4234) may alternatively be pointed. Disassembly feature (4218) is shown as a wedge. While disassembly feature (4218) is shown as having a distal most end (4236) that is pointed, distal most end (4234) may alternatively be blunt. First and second lateral surfaces (4238, 4240) of disassembly feature (4218) extend outwardly and away from distal most end (4236). Disassembly feature (4220) is shown as a torque wrench. Distal most end (4242) may rotate a fastener for disassembly. Disassembly feature (4222) is shown as a screwdriver having a distal most end (4244) configured to rotate a fastener for disassembly. Disassembly feature (4224) is shown as a pipe cleaner. Disassembly feature (4224) may be used to remove debris prior to disassembly features (4214, 4216, 4218, 4220, 4222) be utilized.

Tool (4210) is shown as including a coupling portion (4245) configured to couple with second interface (4042) or third interface (4044). In some versions, disassembly features (4214, 4216, 4218, 4220, 4222, 4224) may be removable from body (4212). In some versions, disassembly features (4214, 4216, 4218, 4220, 4222, 4224) may be injection molded from a single unitary piece. In some versions, disassembly features (4214, 4216, 4218, 4220, 4222, 4224) may be manufactured using exclusively metal or exclusively plastic. In some versions, robotic arms (4028, 4030), tools (4036, 4038) and accompanying disassembly features (4214, 4216, 4218, 4220, 4222, 4224) are not utilized in the normal operation of the surgical instrument (4110), but allow for tools (4036, 4038) to obtain different orientations and access various portions of patient side cart (4012) and/or switch tools (4036, 4038) and disassembly features (4214, 4216, 4218, 4220, 4222, 4224).

1. First Exemplary Disassembly Feature

Figure 9:
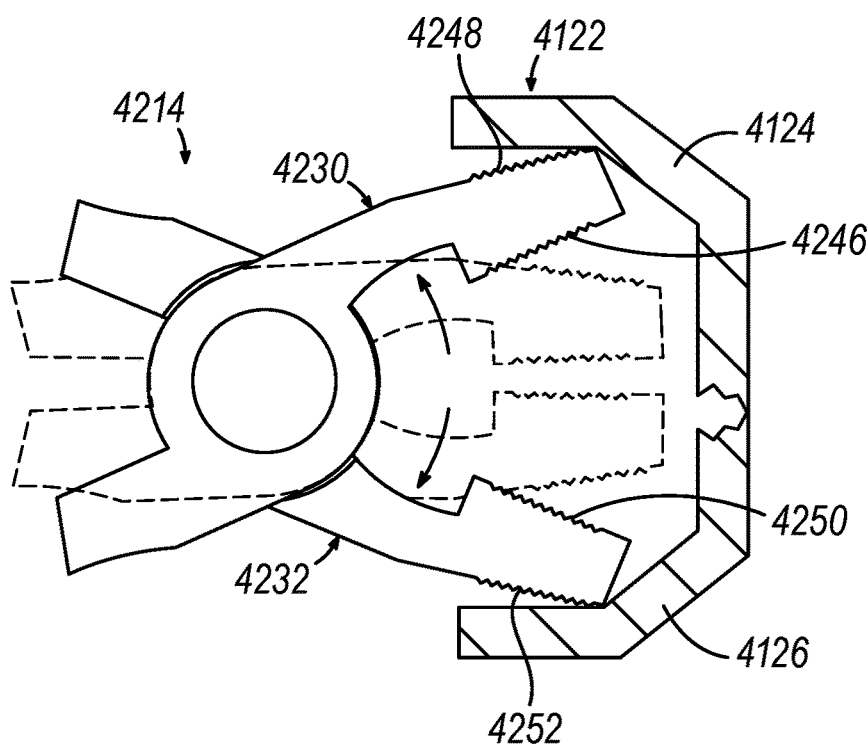
FIG. 9 depicts a side elevational view of a first exemplary disassembly feature of the tool of FIG. 8 moving from a first configuration to a second configuration to disassemble a portion of the tool of FIG. 7.
Figure 10:
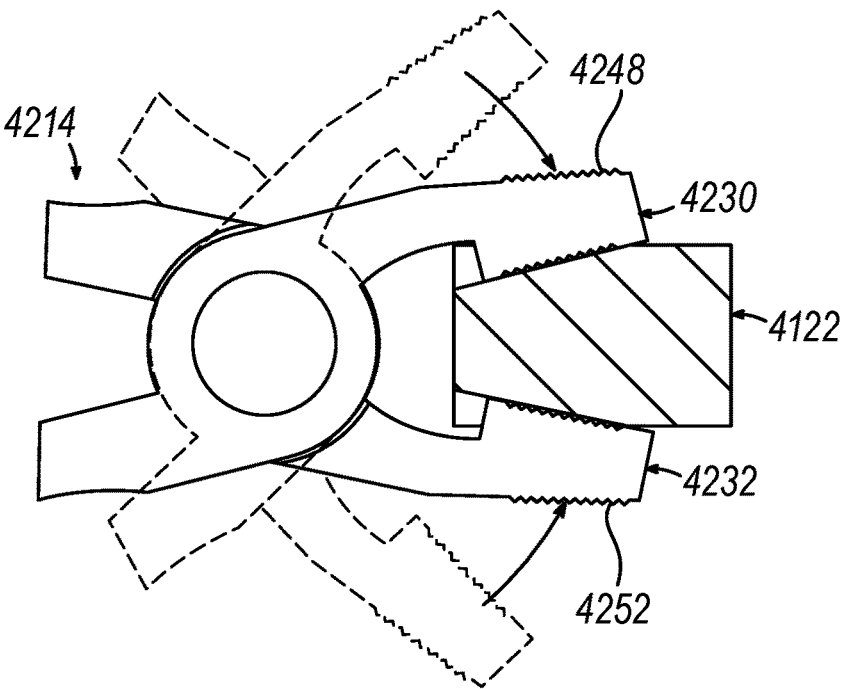
FIG. 10 depicts a side elevational view of the disassembly feature of FIG. 9 moving from a third configuration to a fourth configuration to disassemble a portion of the surgical instrument of FIG. 7.

FIGS. 9-10 show an enlarged view of disassembly feature (4214) of FIG. 8. Particularly, FIG. 9 shows disassembly feature (4214) being used as a reverse pliers to fracture first and second housing portions (4124, 4126) of housing (4122). Opposing first and second jaws (4230, 4232) move from a first configuration (shown in dashed lines) to a second configuration (shown in solid lines) to disassemble housing (4122) of surgical instrument (4110) of FIG. 7. In some versions, only one of first and second jaws (4230, 4232) moves, while the other jaw of first and second jaws (4230, 4232) remains stationary. While distal most ends (4234) of first and second jaws (4230, 4232) are shown as being planar, first and second jaws (4230, 4232) may alternatively terminate to a point. The point may further enable distal most ends (4234) of first and second jaws (4230, 4232) to pry open housing (4122). First jaw (4230) includes inner and outer surfaces (4246, 4248). Similarly, second jaw (4232) includes inner and outer surfaces (4250, 4252). As shown, outer surfaces (4248 4252) of first and second jaws (4230, 4232) push against housing (4122) to fracture housing (4122) or otherwise manipulate housing (4122) as desired.

FIG. 10 shows disassembly feature (4214) of FIG. 9 moving from a third configuration to a fourth configuration to grasp a portion of surgical instrument (4110) of FIG. 7. As shown, inner surfaces (4246, 4250) of first and second jaws (4230, 4232) collectively grab a portion of surgical instrument (4110) as desired. For example, outer surfaces (4248 4252) of first and second jaws (4230, 4232) may be first used to access the desired reclaimable components, then inner surfaces (4246, 4250) of first and second jaws (4230, 4232) may be used to remove and orient the reclaimable components for packaging system (4016). Disassembly feature (4214) may be used to autonomously engage a mechanical key on first robotic arm (4026).

2. Second Exemplary Disassembly Feature

Figure 11A:
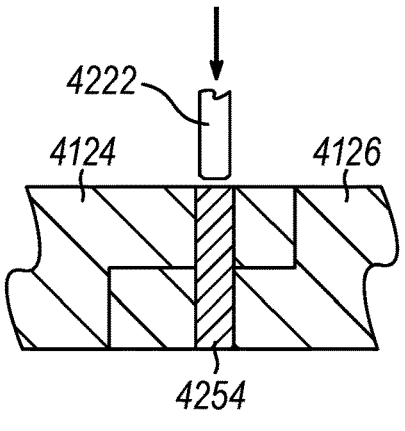
FIG. 11A depicts a schematic sectional view of first and second housing portions of the surgical instrument of FIG. 7 coupled together in a connected configuration using a mechanical connector prior to disassembly by a second exemplary disassembly feature of the tool of FIG. 8.
Figure 11B:
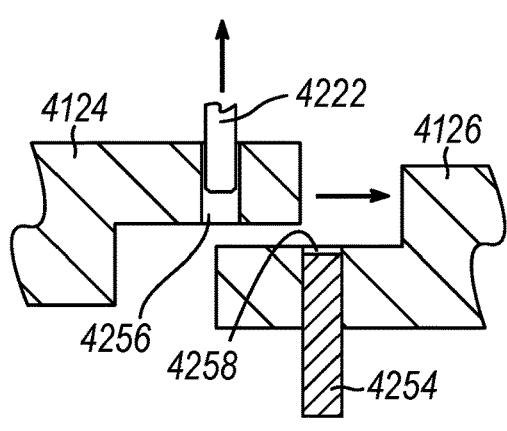
FIG. 11B depicts the schematic sectional view of first and second housing portions similar to FIG. 11A, but after the disassembly feature of FIG. 11A moves the mechanical connector to a non-connected configuration.

FIGS. 11A-11B show first and second housing portions (4124, 4126) of surgical instrument (4110) being disassembled using disassembly feature (4222) of FIG. 8. Particularly, FIG. 11A shows first and second housing portions (4124, 4126) of FIG. 7 coupled together in a connected configuration using a mechanical connector (4254) prior to separation using disassembly feature (4222). FIG. 11B shows first and second housing portions (4124, 4126) of FIG. 11A, but after disassembly feature (4222) of FIG. 11A moves mechanical connector (4254) to a non-connected configuration. Disassembly feature (4222) functions as a mechanical key to release first and second housing portions (4124, 4126) of surgical instrument (4110) to enable self-disassembly. Mechanical connector (4254) slides within slots (4256, 4258) of first and second housing portions (4124, 4126). While disassembly feature (4222) is shown as translating mechanical connector (4254) to disengage first and second housing portions (4124, 4126), disassembly feature (4222) may rotate and/or translate mechanical connector (4254) to disengage first and second housing portions (4124, 4126). Small predefined housing features may prevent inadvertent disassembly, while still allowing tools (4036, 4038) suitable access to first and second housing portions (4124, 4126).

3. Third Exemplary Disassembly Feature

Figure 12A:
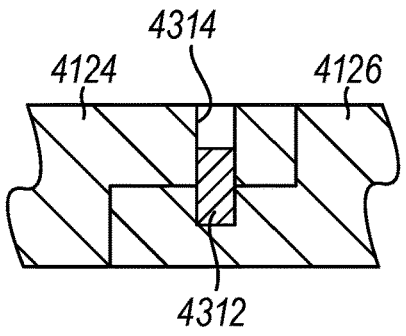
FIG. 12A depicts a schematic sectional view of first and second housing portions of the surgical instrument of FIG. 7 coupled together in a connected configuration using a magnetic connector.
Figure 12B:
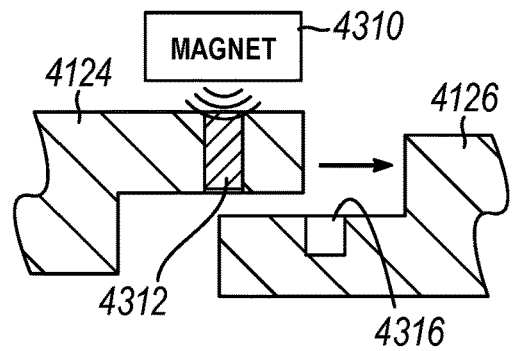
FIG. 12B depicts the schematic sectional view of first and second housing portions similar to FIG. 12A, but after the magnetic connector is moved to a non-connected configuration by a third exemplary disassembly feature.

FIGS. 12A-12B show first and second housing portions (4124, 4126) of surgical instrument (4110) being disassembled using an exemplary disassembly feature (4310), which is shown as a magnet. Disassembly feature (4310) may be included as a standalone tool or may be included in tool (4210). Particularly, FIG. 12A shows first and second housing portions (4124, 4126) of FIG. 7 coupled together in a connected configuration using a magnetic connector (4312) prior to separation by disassembly feature (4310). FIG. 12B shows first and second housing portions (4124, 4126) of FIG. 12A, but after disassembly feature (4310) moves magnetic connector (4312) to a non-connected configuration.

Disassembly feature (4310) functions as a magnetic key to release first and second housing portions (4124, 4126) of surgical instrument (4110) to enable self-disassembly. Magnetic connector (4312) slides within slots (4314, 4316) of first and second housing portions (4124, 4126) between the connected configuration and the non-connected configuration. While disassembly feature (4310) is shown as translating magnetic connector (4312) to disengage first and second housing portions (4124, 4126), disassembly feature (4310) may rotate and/or translate magnetic connector (4312) to disengage first and second housing portions (4124, 4126). While disassembly feature (4310) is shown as attracting magnetic connector (4312), disassembly feature (4310) may alternatively repel magnetic connector (4312).

4. Fourth Exemplary Disassembly Feature

Figure 13A:
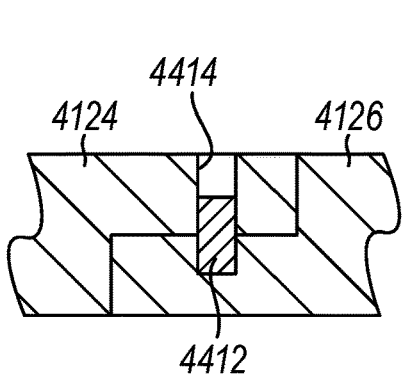
FIG. 13A depicts a schematic sectional view of first and second housing portions of the surgical instrument of FIG. 7 coupled together in a connected configuration using an electrical connector.
Figure 13B:
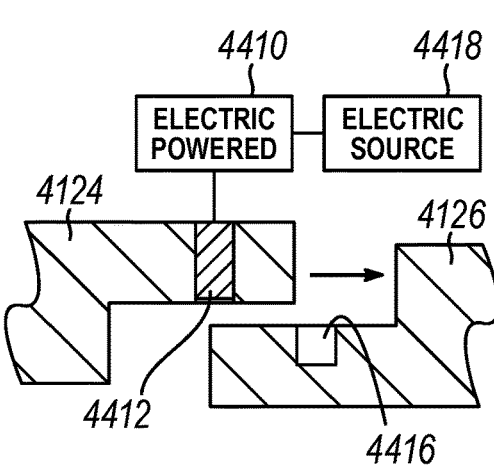
FIG. 13B depicts the schematic sectional view of first and second housing portions similar to FIG. 13A, but after the electrical connector is moved to a non-connected configuration using a fourth exemplary disassembly feature.

FIGS. 13A-13B show first and second housing portions (4124, 4126) of surgical instrument (4110) being disassembled using an exemplary disassembly feature (4410), which is shown as an electrically powered disassembly feature (4410). Disassembly feature (4410) may be included as a standalone tool or may be included in tool (4210). Particularly, FIG. 13A shows first and second housing portions (4124, 4126) of FIG. 7 coupled together in a connected configuration using an electrically movable connector (4412) prior to separation using disassembly feature (4410). FIG. 13B shows first and second housing portions (4124, 4126) of FIG. 13A, but after the disassembly feature (4410) of FIG. 13A moves electrically movable connector (4412) to a non-connected configuration. Electrically movable connector (4412) slides within slots (4414, 4416) of first and second housing portions (4124, 4126).

Disassembly feature (4410) functions as an electrically powered key to release first and second housing portions (4124, 4126) of surgical instrument (4110) to enable self-disassembly. Disassembly feature (4410) is operatively connected to a power source (4418) to provide power to disassembly feature (4410). While disassembly feature (4410) is shown as translating electrically movable connector (4412) to disengage first and second housing portions (4124, 4126), disassembly feature (4410) may rotate and/or translate electrically movable connector (4412) to disengage first and second housing portions (4124, 4126).

5. Fifth Exemplary Disassembly Feature

FIGS. 14A-14B show housing (4122) of surgical instrument (4110) being separated using an exemplary disassembly feature (4510), which is shown as a laser. Disassembly feature (4510) may be included as a standalone tool or may be included in tool (4210). Particularly, FIG. 14A shows housing (4122) in a connected configuration prior to separation by disassembly feature (4510). Housing (4122) includes marker (4132) shown as a recessed portion to direct disassembly feature (4510) to the desired location. FIG. 14B shows housing (4122) already being disconnected after disassembly feature (4510) penetrates completely through housing (4122). Disassembly feature (4510) may cut through specific predetermined areas to release first and second reclaimable components (4128, 4130). In some versions, housing (4122) of surgical instrument (4110) may be formed from nitinol, so that disassembly feature (4510) may apply heat to transform the nitinol material for disassembly.

6. Sixth Exemplary Disassembly Feature

FIGS. 15A-15B show disassembly features (4610, 4612), shown as first and second end effectors configured to interact with tissue of a patient. Disassembly features (4610, 4612) may be operatively coupled with second and third robotic arms (4028, 4030). Disassembly features (4610, 4612) are shown moving from the first configuration toward the second configuration. Disassembly features (4610, 4612) may be similar to end effectors (166, 180, 188, 4116) of surgical instruments (152, 154, 156, 4110). Disassembly features (4610, 4612) each include a pivotable clamp arm (4614, 4616) for grasping. Marker (4132) of housing (4122) highlights a frangible portion (4618). Disassembly features (4610, 4612) are configured to separate frangible portion (4618) of housing (4122) of surgical instrument (4034) of FIG. 7. FIG. 15B shows a front schematic view of the frangible portion (4618) in a severed state.

In some versions, disassembly feature (4610) is configured to provide a first predetermined force, a first predetermined motion, and/or first predetermined task to disconnect at least portion of surgical instrument (4110). In some versions, underapplication of a first predetermined force or overapplication of the first predetermined force does not release housing (4122). The first predetermined force is greater than a maximum force capable of being provided manually by a user. In other words, the first predetermined force may exceed the force that the user is capable of manually exerting to remove housing (4122). In some versions, both underapplication and overapplication prevent housing (4122) from sufficiently opening.

Disassembly feature (4612) is configured to provide a second predetermined force, a second predetermined motion, and/or second predetermined task independent from first predetermined force, first predetermined motion, and/or first predetermined task applied by disassembly feature (4610) to disconnect at least portion of surgical instrument (4034) in response to instructions from controller (4046). Utilization of multiple separate independently applied forces, motions, or tasks collectively allow portions of surgical instrument (4034) to disassemble. For example, disassembly features (4610, 4612) of respective tools (4036, 4038) may produce synchronized motions that cooperatively unlock two or more separate portions simultaneously to open or remove a portion of surgical instrument (4034) that the user would not be able to manually produce the cooperative forces.

D. Exemplary Tool Dispenser

Figure 16:
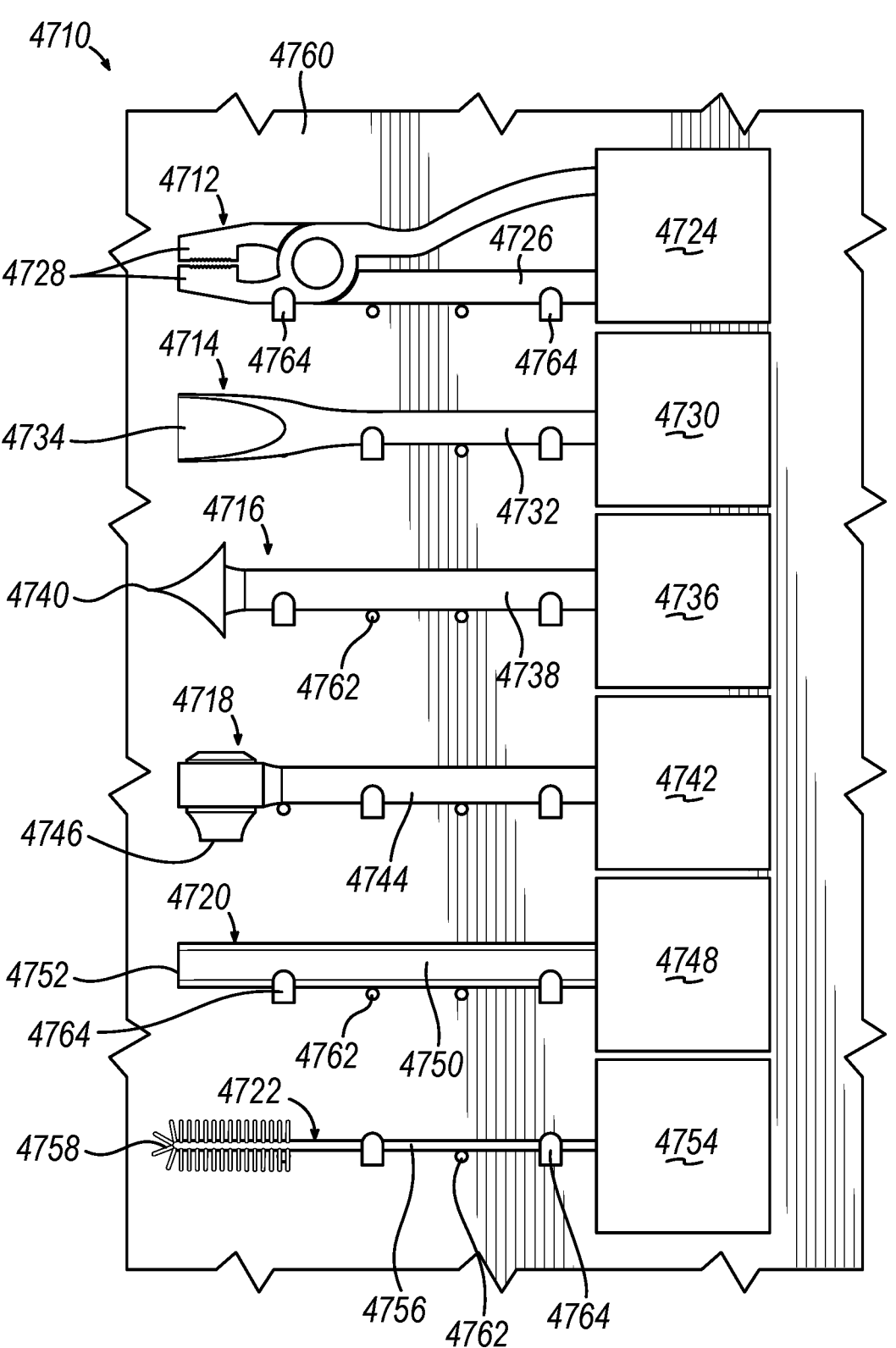
FIG. 16 depicts a side elevational view of a plurality of tools positioned on a tool dispenser.

FIG. 16 shows an exemplary tool dispenser (4710) configured to retain a plurality of tools (shown as tools (4712, 4714, 4716, 4718, 4720, 4722)). Tools (4712, 4714, 4716, 4718, 4720, 4722) may be individually wrapped in sterile packaging. Tool (4712) includes a coupling portion (4724), a shaft (4726), and a disassembly feature (4728), which is similar to disassembly feature (4214) shown in FIGS. 8-10. Tool (4714) includes a coupling portion (4730), a shaft (4732), and a disassembly feature (4734), which is similar to disassembly feature (4216) shown in FIG. 8. Tool (4716) includes a coupling portion (4736), a shaft (4738), and a disassembly feature (4740), which is similar to disassembly feature (4218) shown in FIG. 8. Tool (4718) includes a coupling portion (4742), a shaft (4744), and a disassembly feature (4746), which is similar to disassembly feature (4220) shown in FIG. 8. Tool (4720) includes a coupling portion (4748), a shaft (4750), and a disassembly feature (4752), which is similar to disassembly feature (4222) shown in FIG. 8. Tool (4722) includes a coupling portion (4754), a shaft (4756), and a disassembly feature (4758), which is similar to disassembly feature (4224) shown in FIG. 8.

Coupling portions (4724, 4730, 4736, 4742, 4748, 4754) are configured to couple with second interface (4042) of robotic arm (4028) or third interface (4044) of robotic arm (4030) shown in FIG. 6. In some versions, coupling portions (4724, 4730, 4736, 4742, 4748, 4754) may have a base in the shape of an X cross-sectional pattern or a T cross-sectional pattern. The user may attach coupling portions (4724, 4730, 4736, 4742, 4748, 4754) of tools (4712, 4714, 4716, 4718, 4720, 4722) to second interface (4042) or third interface (4044) based on surgical instrument (4034) to be disassembled.

Tools (4712, 4714, 4716, 4718, 4720, 4722) may hang on tool dispenser (4710) for subsequent retrieval. As shown, tool dispenser (4710) includes a pegboard (4760) that includes recessed portions or apertures (4762) that support projections (4764). Projections (4764) support tools (4712, 4714, 4716, 4718, 4720, 4722). However, a variety of suitable tool dispensers are also envisioned. While tools (4712, 4714, 4716, 4718, 4720, 4722) are shown as extending horizontally, tools (4712, 4714, 4716, 4718, 4720, 4722) may alternatively be arranged at a variety of other angles to be received by robotic arms (4028, 4030). Tools (4712, 4714, 4716, 4718, 4720, 4722) may be selected by controller (4046) for disassembly of surgical instrument (4034) based disassembly instructions. Disassembly instructions may be transmitted to controller (4046) or another portion of robotic surgical system (4010). Disassembly instructions may be disposed on packaging materials as shown and described below with reference to FIG. 17.

E. Exemplary Surgical Kit

Figure 17:
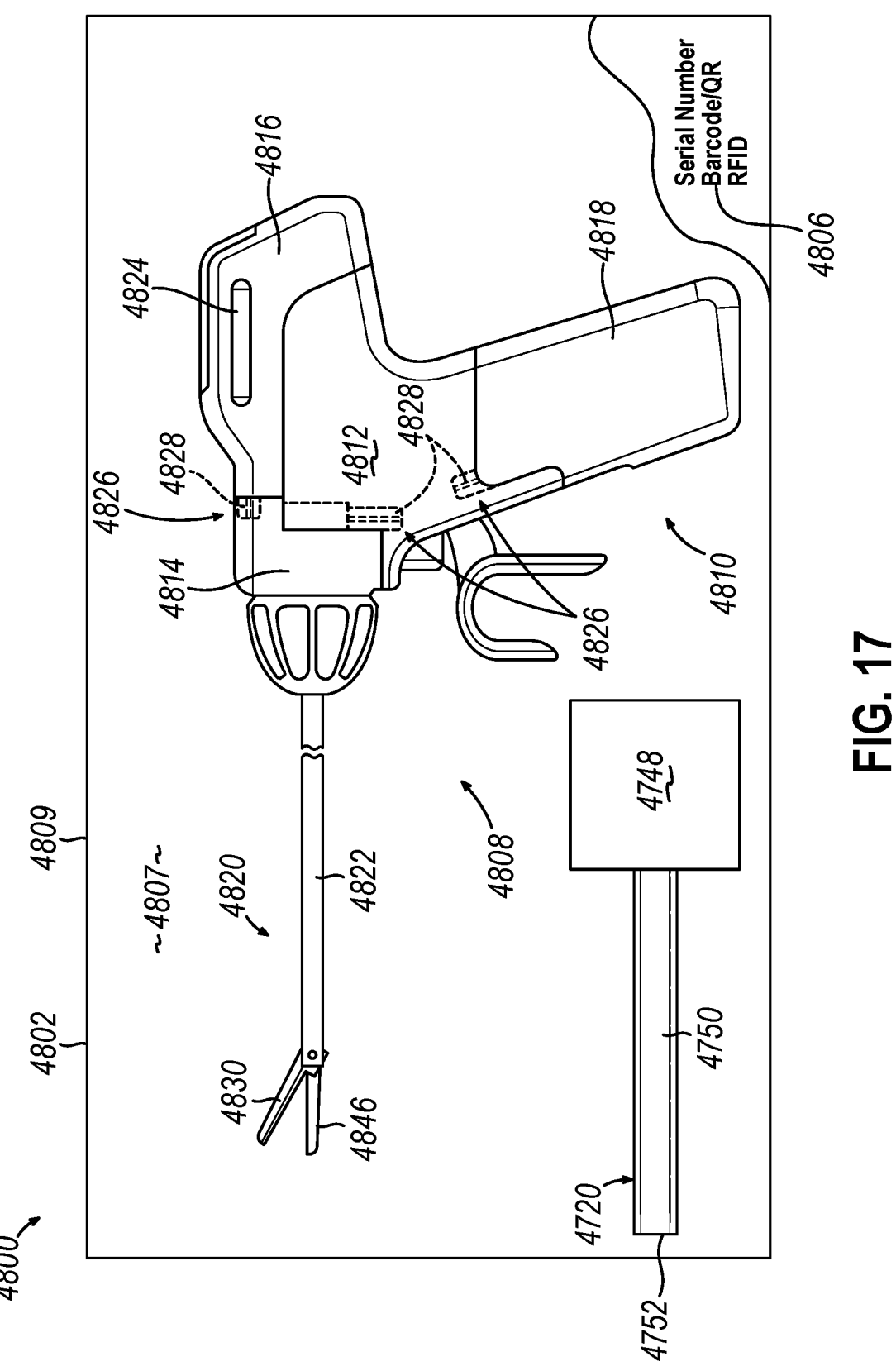
FIG. 17 depicts an exemplary surgical kit that includes packaging surrounding another exemplary surgical instrument and a disassembly feature.

FIG. 17 shows an exemplary surgical kit (4800) that includes a packaging (4802), tool (4720), instrument information (4806), and a surgical instrument (4808). Packaging defines an interior (4807) and an exterior (4809). For example, surgical kit (4800) may contain both a surgical instrument (4110) as well as tool (4036, 4038) for coupling and/or decoupling surgical instrument (4808) from robotic surgical system (4010). Surgical kit (4800) may include a variety of surgical instruments (112, 152, 154, 156, 4034, 4110) and tools (4036, 4038, 4210, 4712, 4714, 4716, 4718, 4720, 4722). Instrument information (4806) may be in the form disassembly instructions to indicate to the desired position and/or orientation of surgical instrument (4808) for disassembly and/or a computer readable code that may be read and interpreted by controller (4046).

Surgical instrument (4808) may be similar to surgical instruments (112, 152, 154, 156). Surgical instrument (4808) may be configured to deliver ultrasonic energy, Radio Frequency ("RF") energy, or both. Surgical instrument (4808) may be configured to be hand-held or fitted with a corresponding portion of a robotic arm (see FIG. 7). Surgical instrument (4808), like surgical instruments (112, 152, 154, 156), includes a body assembly (4810), a shaft assembly (4820), and an end effector (4830). Shaft (4822) of shaft assembly (4820) extends distally from body assembly (4810) to end effector (4830). Surgical instrument (4808) differs from surgical instruments (112, 152, 154, 156) in that surgical instrument (4808) includes body assembly (4810) configured to be easily disassembled to expose at least one of a plurality of internal components for removal into separate waste streams. Surgical instrument (4808) is configured to deliver ultrasonic energy similar to surgical instrument (152). Body assembly (4810) surrounds a portion of an energy drive system (4840) and a portion of a circuit assembly (4850). Energy drive system (4840) includes an ultrasonic transducer (4842), a waveguide (4844), and an ultrasonic blade (4846). Energy drive system (4840) may further include a battery (4848), or a generator (150) (see FIG. 5) configured to supply energy. Ultrasonic transducer (4842) is proximally positioned within body assembly (4810) and extends distally to waveguide (4844). Waveguide (4844) extends distally through shaft assembly (4820) to ultrasonic blade (4846). Circuit assembly (4850) includes a main circuit board (4852), a memory member (4854), and a controller (4856). Reclaimable components may include portions of body assembly (4810), shaft assembly (4820) and/or end effector (4830), including components of energy drive system (4840).

Body assembly (4810) includes a plurality of selectively removeable shroud portions (4812, 4814, 4816, 4818). Shroud portions (4812, 4814, 4816, 4818) are configured to provide support for energy drive system (4840), shaft assembly (4820), and circuit assembly (4850). As illustrated, shroud portions (4812, 4814, 4816, 4818) include a first shroud portion (4812), a second shroud portion (4814), a third shroud portion (4816), and a fourth shroud portion (4818), but may include any number of shroud portions (4812, 4814, 4816, 4818) that inhibit access to circuit assembly (4850) and energy drive system (4840). Each shroud portion (4812, 4814, 4816, 4818) is removably affixed to another shroud portion (4812, 4814, 4816, 4818). Users may remove a shroud portion (4812, 4814, 4816, 4818) to provide access to portions of energy drive system (4840) and portions of circuit assembly (4850) in a disconnected state (see FIG. 6B). Once accessed, portions of energy drive system (4840) and portions of circuit assembly (4850) may be disposed of in separate waste streams. Shroud portions (4812, 4814, 4816, 4818) may include gripping features (4824). Shroud portions (4812, 4814, 4816, 4818) further include a plurality of alignment features (4826) configured to align each shroud portion (4812, 4814, 4816, 4818) with an adjacent shroud portion (4812, 4814, 4816, 4818). Alignment features (4826) in one example include a key (4828) and a keyway (4832). Key (4828) is sized to slide within keyway (4832).

Figure 18:
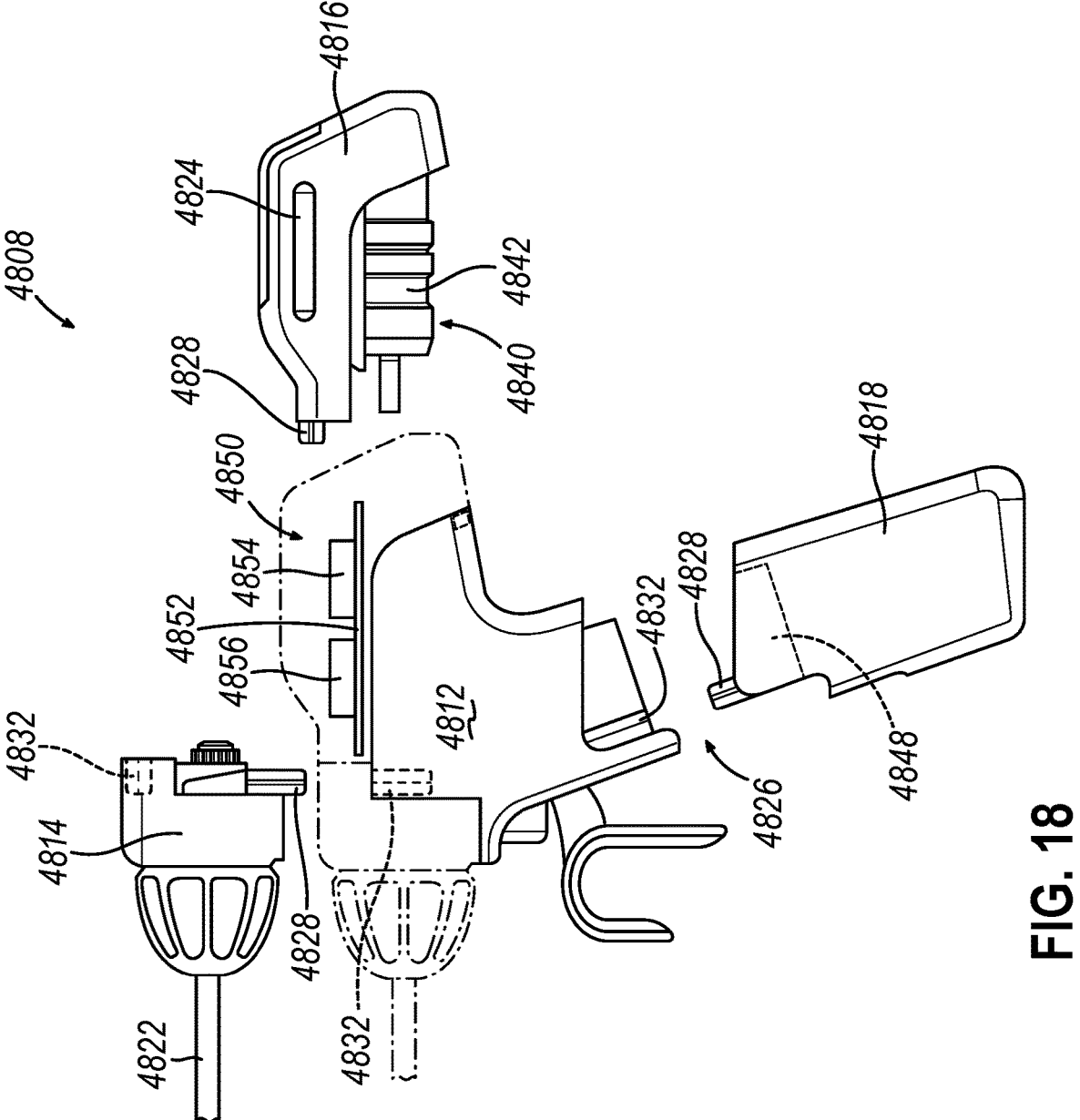
FIG. 18 depicts the surgical instrument of FIG. 17 but in a disassembled configuration.

FIG. 18 shows surgical instrument (4808) of FIG. 17, but after being removed from packaging (4802) of surgical kit (4800) and after disassembly using disassembly feature (4804) that was included in the same packaging (4802) of surgical kit (4800). In the disconnected state, shroud portions (4812, 4814, 4816, 4818) are separated from one another. Removal of shroud portions (4812, 4814, 4816, 4818) facilitates access to and removal at least a portion of energy drive system (4840) and/or at least a portion of circuit assembly (4850).

F. Exemplary Method

Figure 19:
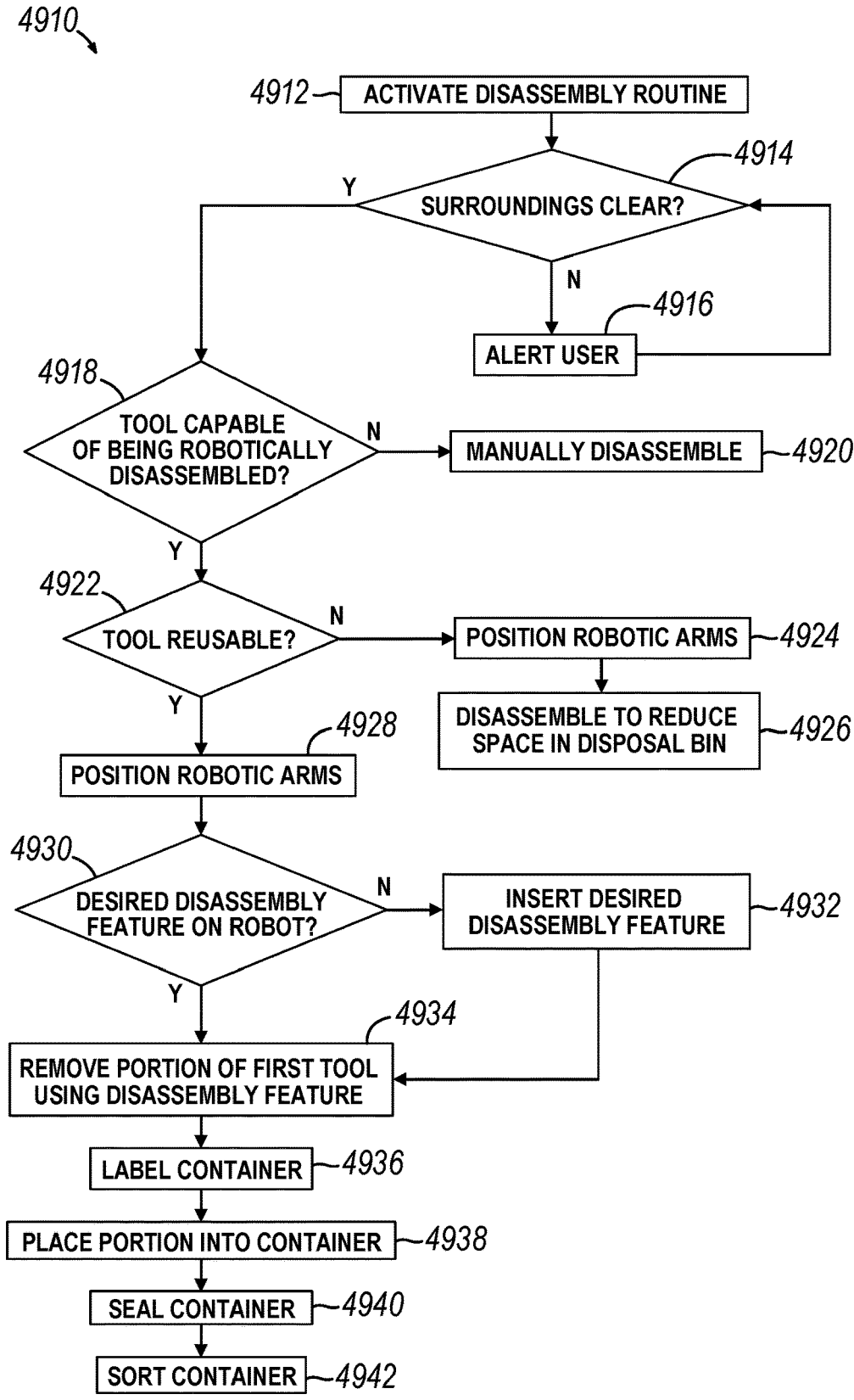
FIG. 19 depicts a diagrammatic view of an exemplary method of operating the robotic surgical system of FIG. 6.

FIG. 19 shows a diagrammatic view of an exemplary method (4910) of disassembling the robotic surgical system (4010) of FIG. 6. Method (4910) may include steps (4912, 4914, 4916, 4918, 4920, 4922, 4924, 4926, 4928, 4930, 4932, 4934, 4936, 4938, 4940, 4942). However, more or fewer steps are also envisioned.

At step (4912), method (4910) includes activating the disassembly routine. In some versions, once the disassembly routine is activated, the remainder of the steps may be performed autonomously without any interaction by the user. For example, at the end of a procedure, the autonomous system may react to user input to disassemble surgical instrument (4034). Particularly, a device code may be received by controller (4046), controller (4046) interprets disassembly instructions based on surgical instrument (112, 152, 154, 156, 4034, 4110, 4808). Markers (4132) of surgical instrument (4110) may be used to aid patient side cart (4012) in locating the predetermined disassembly location. For example, at least one of first and second housing portions (4124, 4126) may include markers (4132) to indicate to robot the position/orientation of surgical instrument (112, 152, 154, 156, 4034, 4110, 4808). In some versions, controller (4046) may sense information pertaining to surgical instrument (112, 152, 154, 156, 4034, 4110, 4808), such that the act of disassembling is performed based on sensing with or without subsequent user intervention.

At step (4914), method (4910) includes determining if the surroundings are clear. Controller (4046) checks available contextual information prior to disassembly. For example, controller (4046) may verify the patient is off the operating table (4024) and staff are located a safe position away from robotic surgical system. This determination may be performed using at least one of sensor (4048) in operating room (116), badge proximity scanners, a laparoscopic camera, and a weight sensor on operating table (4024). Badge proximity scanners may assess whether users are present within operating room (116) and where they are located within operating room (116). If the surroundings are not clear, at step (4916), controller (4046) may alert the user. The user may manually clear the alert or robotic surgical system (4010) may continuously or periodically assess whether the surroundings (e.g., within operating room (116)) are clear.

If the surroundings are clear, at step (4918), method (4910) may determine if surgical instrument (4034) is capable of being robotically disassembled. Robotic surgical system (4010) provides feedback for which surgical instruments (112, 152, 154, 156, 4034, 4110, 4808) may be disassembled and instructs the user to attach any of surgical instruments (112, 152, 154, 156, 4034, 4110, 4808) and tools (4036, 4038, 4210, 4712, 4714, 4716, 4718, 4720, 4722) to first, second and third robotic arms (4026, 4028, 4030). If surgical instrument (112, 152, 154, 156, 4034, 4110, 4808) is not capable of being robotically disassembled, at step (4920), surgical instrument (4034) may be manually disassembled. For components of surgical instruments that cannot be disassembled by tools (4036, 4038, 4210, 4712, 4714, 4716, 4718, 4720, 4722) of second and third robotic arms (4028, 4030), manual instructions may be displayed through monitors located within operating room (116).

In some versions, a first surgical instrument (112, 152, 154, 156, 4034, 4110, 4808) has a first keying and a second surgical instrument (112, 152, 154, 156, 4034, 4110, 4808) has a second keying; controller (4046) of robotic surgical system (4010) accesses a lookup table that informs controller (4046) which of the key patterns to use for surgical instrument (112, 152, 154, 156, 4034, 4110, 4808). For example, a first-generation device may utilize a first disassembly protocol or program. A second-generation device has an architecture that differs from the first generation device. Robotic surgical system (4010) may identify tools (4036, 4038, 4210, 4712, 4714, 4716, 4718, 4720, 4722) uniquely and select the desired disassembly method for the desired generation of surgical instrument (112, 152, 154, 156, 4034, 4110, 4808).

If surgical instrument (112, 152, 154, 156, 4034, 4110, 4808) is capable of being robotically disassembled, at step (4922), controller (4046) may determine if surgical instrument (112, 152, 154, 156, 4034, 4110, 4808) is reusable. During disassembly, robotic surgical system (4010) recognizes the appropriate reclamation and disposal methods for surgical instrument (112, 152, 154, 156, 4034, 4110, 4808) and components contained therein. Robotic surgical system (4010) may optionally perform mechanical and/or electrical tests to determine if surgical instrument (112, 152, 154, 156, 4034, 4110, 4808) is capable of to be reused or recertified. Controller (4046) is configured to perform at least one mechanical or electrical test on surgical instrument (112, 152, 154, 156, 4034, 4110, 4808) to determine reusability of surgical instrument (112, 152, 154, 156, 4034, 4110, 4808). Sensor (4048) is configured to sense an area around robotic surgical system (4010). If surgical instrument (112, 152, 154, 156, 4034, 4110, 4808) is not reusable, at step (4924), controller (4046) may instruct first, second, and third robotic arms (4026, 4028, 4030) to desired position. At step (4926), if surgical instrument (112, 152, 154, 156, 4034, 4110, 4808) is not able to be reused, patient side cart (4012) upon instruction from controller (4046) dismantles surgical instrument (4110) to reduce space in disposal apparatus (4060). This may assist in environmentally friendly disposal of components as instructed.

If surgical instrument (112, 152, 154, 156, 4034, 4110, 4808) is reusable, at step (4928), controller (4046) may instruct first, second, and third robotic arms (4026, 4028, 4030) to move the desired position. This predetermined position may aid in the removal of surgical instrument (112, 152, 154, 156, 4034, 4110, 4808). Robotic surgical system (4010) properly positions tools (4036, 4038, 4210, 4712, 4714, 4716, 4718, 4720, 4722) so that first, second, and third robotic arms (4026, 4028, 4030) do not collide, and so that surgical instrument (112, 152, 154, 156, 4034, 4110, 4808) and tools (4036, 4038, 4210, 4712, 4714, 4716, 4718, 4720, 4722) are properly positioned to interact with one another.

After positioning first, second, and third robotic arms (4026, 4028, 4030), at step (4930), controller (4046) may identify the desired disassembly features (4050, 4052, 4214, 4216, 4218, 4220, 4222, 4224, 4310, 4410, 4510, 4610, 4612, 4728, 4734, 4740, 4746, 4752, 4758) and determine if the desired disassembly features (4050, 4052, 4214, 4216, 4218, 4220, 4222, 4224, 4310, 4410, 4510, 4610, 4612, 4728, 4734, 4740, 4746, 4752, 4758) is currently coupled with robotic arms (4028, 4030). If the desired disassembly feature (4050, 4052, 4214, 4216, 4218, 4220, 4222, 4224, 4310, 4410, 4510, 4610, 4612, 4728, 4734, 4740, 4746, 4752, 4758) is not currently coupled with robotic arm (4028, 4030), at step (4932), controller (4046) may instruct second and third robotic arms (4028, 4030) to couple with desired tool (4036, 4038, 4210, 4712, 4714, 4716, 4718, 4720, 4722) that include the desired disassembly features (4050, 4052, 4214, 4216, 4218, 4220, 4222, 4224, 4310, 4410, 4510, 4610, 4612, 4728, 4734, 4740, 4746, 4752, 4758).

If the desired disassembly feature(s) (4050, 4052, 4214, 4216, 4218, 4220, 4222, 4224, 4310, 4410, 4510, 4610, 4612, 4728, 4734, 4740, 4746, 4752, 4758) is currently coupled with robotic arms (4028, 4030) of patient side cart (4012), at step (4934), controller (4046) may instruct robotic arms (4028, 4030) to remove a portion of surgical instrument (112, 152, 154, 156, 4034, 4110, 4808) using disassembly features (4050, 4052, 4214, 4216, 4218, 4220, 4222, 4224, 4310, 4410, 4510, 4610, 4612, 4728, 4734, 4740, 4746, 4752, 4758). Regarding surgical instrument (4808), reclaimable components may include portions of body (4112), shaft assembly (4114) and/or end effector (4116), including ultrasonic components. Regarding surgical instrument (4808), reclaimable components may include portions of body assembly (4810), shaft assembly (4820) and/or end effector (4830), including components of energy drive system (4840). Tool (4036) (and optionally tool (4038)) may apply a predetermined force, motion, or stroke to overcome a connection bias of surgical instrument (112, 152, 154, 156, 4034, 4110, 4808). A portion of surgical instrument (112, 152, 154, 156, 4034, 4110, 4808) may be disassembled using disassembly features (4050, 4052, 4214, 4216, 4218, 4220, 4222, 4224, 4310, 4410, 4510, 4610, 4612, 4728, 4734, 4740, 4746, 4752, 4758) of tool (4036, 4038, 4210, 4712, 4714, 4716, 4718, 4720, 4722) in response to instructions from controller (4046).

At step (4936), controller (4046) may label package (4066) using labeling device (4054). In some versions, controller (4046) and may assign and labeling device (4054) print label (4064) denoting one or more characteristics of reclaimable portion (4124, 4126). Package (4066) may be pre-labeled, or labels (4064) may be printed from labeling device (4054), which may be part of packaging system (4016) or hub (4014). In some versions, hub (4014) may recognize reclaimable components (4128, 4130) being bagged and dispense appropriate bags and labels.

At step (4938), controller (4046) may instruct second robotic arm (4028) and tool (4036, 4038, 4210, 4712, 4714, 4716, 4718, 4720, 4722) to place portion into a predetermined container. Robotic surgical system (4010) may place reclaimable components (4128, 4130) into the appropriate package (4066). Reclamation containers of different types are positioned alongside patient side cart (4012) to provide operating room personnel with ease of use and increased efficiency. Robotic surgical system (4010) may autonomously detect disposal apparatus (4060) and first and second shipping containers (4068, 4070). In some versions, an algorithm of controller (4046) may identify a bag station location and autonomously move reclaimable components (4128, 4130) to appropriate position. Packaging device (4056), which may include a bag dispenser configured to dispense flexible bags, interacts with controller (4046) such that robotic arms (4028, 4030) locate package (4066) that is automatically dispensed, opened, and closed when reclaimable components (4128, 4130) are positioned therein. Autonomously bagging and sealing may aid in proper disposition post-surgery.

At step (4940), method (4910) may also include sealing package (4066) that contains portion (e.g., reclaimable components (4128, 4130)) of surgical instrument (112, 152, 154, 156, 4034, 4110, 4808) using sealing device (4058) in response to instructions from controller (4046). For example, controller (4046) may instruct second robotic arm (4028) and tool (4036, 4038, 4210, 4712, 4714, 4716, 4718, 4720, 4722) and/or third robotic arm (4030) and tool (4036, 4038, 4210, 4712, 4714, 4716, 4718, 4720, 4722)) to seal package (4066). Sealing device (4058) may vacuum seal and/or heat seal reclaimable components (4128, 4130) of surgical instrument (112, 152, 154, 156, 4034, 4110, 4808) post procedure within packages (4066) to prevent cross contamination and reduce space around packaging system (4016).

At step (4942), controller (4046) may sort packages (4066) by desired location/destination. Robotic surgical system (4010) may utilize location-based information to incorporate different disposal and shipping instructions based on country or regional differences and/or specific medical facility capabilities. Reclaimable components (4128, 4130) in packages (4066) and disposable components in disposal apparatus (4060) may be sorted and disposed in different ways depending on the local regulations.

III. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A robotic surgical system comprising: (a) a controller; (b) a surgical instrument configured to interact with a patient, wherein the surgical instrument is operatively coupled with the controller; and (c) a tool operatively coupled with the robotic surgical system, wherein the tool includes a disassembly feature, wherein the disassembly feature of the tool is configured to disconnect at least a portion of the surgical instrument from the robotic surgical system in response to instructions from the controller.

Example 2

The surgical system of Example 1, wherein the surgical instrument includes a housing, wherein the disassembly feature includes at least one of a magnetic key, an electrical key, or a mechanical key to release the housing.

Example 3

The robotic surgical system of any of Examples 1 through 2, wherein the surgical instrument includes a housing, wherein the disassembly feature includes at least one of a torque wrench, a wedge, a reverse pliers, a scraper, or a laser to remove at least the portion of the housing.

Example 4

The robotic surgical system of any of Examples 2 through 3, wherein the disassembly feature is configured to apply a first predetermined force, a first predetermined motion, or first predetermined task to disconnect at least the portion of the surgical instrument.

Example 5

The robotic surgical system of Example 4, wherein the first predetermined force is greater than a maximum force provided manually by a user.

Example 6

The robotic surgical system of any of Examples 4 through 5, wherein the portion of the surgical instrument includes a housing, wherein underapplication of the first predetermined force or overapplication of the first predetermined force does not release the housing.

Example 7

The robotic surgical system of any of Examples 4 through 6, wherein the disassembly feature is configured to apply a second predetermined force, a second predetermined motion, or second predetermined task independent from the first predetermined force, the first predetermined motion, or the first predetermined task to disconnect at least the portion of the surgical instrument in response to the instructions from the controller.

Example 8

The robotic surgical system of any of Examples 4 through 6, further comprising a second tool that includes a second disassembly feature configured to apply a second predetermined force, a second predetermined motion, or second predetermined task independent from the first predetermined force, the first predetermined motion, or the first predetermined task to disconnect at least the portion of the surgical instrument in response to the instructions from the controller.

Example 9

The robotic surgical system of any of Examples 1 through 8, further comprising a package, wherein the package is configured to receive the portion of the surgical instrument in response to the instructions from the controller.

Example 10

The robotic surgical system of Example 9, further comprising a sealing device configured to seal the package after the portion of the surgical instrument is received by the package in response to the instructions from the controller.

Example 11

The robotic surgical system of any of Examples 1 through 10, wherein the tool includes an end effector configured to interact with tissue of the patient, wherein the disassembly feature includes the end effector.

Example 12

The robotic surgical system of any of Examples 1 through 11, wherein the surgical instrument includes an ultrasonic surgical instrument, wherein the ultrasonic surgical instrument includes an ultrasonic component, wherein the controller is configured to autonomously instruct the disassembly feature to disconnect the ultrasonic component from the ultrasonic surgical instrument.

Example 13

The robotic surgical system of any of Examples 1 through 12, further comprising a sensor configured to sense an area around the robotic surgical system, wherein the controller is configured to instruct the disassembly feature of the tool to disconnect at least the portion of the surgical instrument from the robotic surgical system in response to feedback received from the sensor.

Example 14

The robotic surgical system of any of Examples 1 through 13, wherein the controller is configured to perform at least one mechanical or electrical test on the surgical instrument to determine reusability of the surgical instrument.

Example 15

The robotic surgical system of any of Examples 1 through 14, further comprising: (a) a base; (b) a first robotic arm extending outwardly from the base, wherein the first robotic arm is operatively coupled with the surgical instrument; and (c) a second robotic arm extending outwardly from the base, wherein the second robotic arm is coupled with the tool.

Example 16

A robotic surgical system comprising: (a) a base; (b) a controller; (c) a first robotic arm extending outwardly from the base; (d) a surgical instrument configured to interact with a patient, wherein the surgical instrument is operatively coupled with the first robotic arm; (e) a second robotic arm extending outwardly from the base; and (f) a tool operatively coupled with the second robotic arm, wherein the tool includes a disassembly feature configured to disconnect at least a portion of the surgical instrument from the robotic surgical system in response to instructions from the controller.

Example 17

A method of disassembling a robotic surgical system, wherein the robotic surgical system includes a controller, first and second robotic arms, a surgical instrument, and a tool, wherein the first robotic arm is operatively coupled with the surgical instrument, wherein the tool is in communication with the controller, the method comprising: disassembling a portion of the surgical instrument that is operatively coupled the first robotic arm using a disassembly feature of the tool that is operatively coupled second robotic arm.

Example 18

The robotic surgical system of Example 17, wherein the act of disassembling further comprises autonomously applying a predetermined force, motion, or stroke to overcome a connection bias of the surgical instrument.

Example 19

The robotic surgical system of any of Examples 17 through 18, further comprising identifying the tool to perform the act of disassembly in response to the instructions from the controller, and subsequently disassembling the portion of the surgical instrument response to the instructions from the controller.

Example 20

The robotic surgical system of any of Examples 17 through 19, further comprising in response to the instructions from the controller: (a) inserting at least a portion of the surgical instrument into a package; and (b) sealing the package that contains the portion of the surgical instrument using a sealing apparatus.

IV. MISCELLANEOUS

Versions of the devices described above may have application in conventional medical treatments and procedures conducted by a medical professional, as well as application in robotic-assisted medical treatments and procedures.

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

In addition to the foregoing, the teachings herein may be readily combined with the teachings of U.S. patent application Ser. No. 17/854,065, entitled "Method of Reclaiming Portions of Surgical Instruments for Remanufacturing and Sustainability," filed on Jun. 20, 2022, published as U.S. Pat. Pub. No. 2024/0006048 on Jan. 4, 2024, the disclosure of which is incorporated by reference herein. Various suitable ways in which the teachings herein may be combined with the teachings of U.S. patent application Ser. No. 17/854,065 will be apparent to those of ordinary skill in the art in view of the teachings herein.

In addition to the foregoing, the teachings herein may be readily combined with the teachings of U.S. patent application Ser. No. 17/854,050, entitled "Surgical Instrument with Predetermined Separation Features for Waste Stream Utilization and Related Methods," filed on Jun. 20, 2022, published as U.S. Pat. Pub. No. 2024/0000474 on Jan. 4, 2024, the disclosure of which is incorporated by reference herein. Various suitable ways in which the teachings herein may be combined with the teachings of U.S. patent application Ser. No. 17/854,050 will be apparent to those of ordinary skill in the art in view of the teachings herein.

In addition to the foregoing, the teachings herein may be readily combined with the teachings of U.S. patent application Ser. No. 17/854,166, entitled "Surgical Instrument with Removable Cable and Associated Couplings," filed on Jun. 20, 2022, issued as U.S. Pat. No. 12,218,459 on Feb. 4, 2025, the disclosure of which is incorporated by reference herein. Various suitable ways in which the teachings herein may be combined with the teachings of U.S. patent application Ser. No. 17/854,166 will be apparent to those of ordinary skill in the art in view of the teachings herein.

In addition to the foregoing, the teachings herein may be readily combined with the teachings of U.S. patent application Ser. No. 17/854,641, entitled "Surgical System and Methods of Assembly and Disassembly of Surgical Instrument," filed on Jun. 20, 2022, issued as U.S. Pat. No. 12,490,999 on Dec. 9, 2025, the disclosure of which is incorporated by reference herein. Various suitable ways in which the teachings herein may be combined with the teachings of U.S. patent application Ser. No. 17/854,641 will be apparent to those of ordinary skill in the art in view of the teachings herein.

In addition to the foregoing, the teachings herein may be readily combined with the teachings of U.S. patent application Ser. No. 17/854,110, entitled "System for Determining Disposal of Surgical Instrument and Related Methods," filed on Jun. 20, 2022, published as U.S. Pat. Pub. No. 2024/0001416 on Jan. 4, 2024, the disclosure of which is incorporated by reference herein. Various suitable ways in which the teachings herein may be combined with the teachings of U.S. patent application Ser. No. 17/854,110 will be apparent to those of ordinary skill in the art in view of the teachings herein.

In addition to the foregoing, the teachings herein may be readily combined with the teachings of U.S. patent application Ser. No. 17/854,114, entitled "Reclamation Packaging for Surgical Instrument and Related Methods," filed on Jun. 20, 2022, issued as U.S. Pat. No. 12,478,418 on Nov. 25, 2025, the disclosure of which is incorporated by reference herein. Various suitable ways in which the teachings herein may be combined with the teachings of U.S. patent application Ser. No. 17/854,114 will be apparent to those of ordinary skill in the art in view of the teachings herein.

In addition to the foregoing, the teachings herein may be readily combined with the teachings of U.S. patent application Ser. No. 17/854,120, entitled "Surgical Instrument with Various Alignment Features and Methods for Improved Disassembly and Assembly," filed on Jun. 20, 2022, published as U.S. Pat. Pub. No. 2024/0000475 on Jan. 4, 2024, the disclosure of which is incorporated by reference herein. Various suitable ways in which the teachings herein may be combined with the teachings of U.S. patent application Ser. No. 17/854,120 will be apparent to those of ordinary skill in the art in view of the teachings herein.

In addition to the foregoing, the teachings herein may be readily combined with the teachings of U.S. patent application Ser. No. 17/854,127, entitled "Surgical System and Methods for Instrument Assessment and Cleaning," filed on Jun. 20, 2022, published as U.S. Pat. Pub. No. 2024/0003820 on Jan. 4, 2024, the disclosure of which is incorporated by reference herein. Various suitable ways in which the teachings herein may be combined with the teachings of U.S. patent application Ser. No. 17/854,127 will be apparent to those of ordinary skill in the art in view of the teachings herein.

It should also be understood that any ranges of values referred to herein should be read to include the upper and lower boundaries of such ranges. For instance, a range expressed as ranging "between approximately 1.0 inches and approximately 1.5 inches" should be read to include approximately 1.0 inches and approximately 1.5 inches, in addition to including the values between those upper and lower boundaries.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A robotic surgical system comprising:
(a) a controller;
(b) a surgical instrument configured to interact with a patient, wherein the surgical instrument is operatively coupled with the controller;
(c) a tool operatively coupled with the robotic surgical system, wherein the tool includes a disassembly feature, wherein the disassembly feature of the tool is configured to disconnect at least a portion of the surgical instrument from the robotic surgical system in response to instructions from the controller; and
(d) a sensor in communication with the controller, wherein the sensor is a proximity sensor configured to provide feedback to the controller based on a detection of objects in an operating room, wherein the controller is configured to instruct the disassembly feature to disconnect at least the portion of the surgical instrument from the robotic surgical system in response to the feedback based on the detection of objects in an operating room received from the sensor.

2. The robotic surgical system of claim 1, wherein the surgical instrument includes a housing, wherein the disassembly feature includes at least one of a magnetic key, an electrical key, or a mechanical key to release the housing.

3. The robotic surgical system of claim 1, wherein the surgical instrument includes a housing, wherein the disassembly feature includes at least one of a torque wrench, a wedge, a reverse pliers, a scraper, or a laser to remove at least the portion of the housing.

4. The robotic surgical system of claim 1, wherein the disassembly feature is configured to apply a first predetermined force, a first predetermined motion, or first predetermined task to disconnect at least the portion of the surgical instrument.

5. The robotic surgical system of claim 4, wherein the disassembly feature is configured to apply the first predetermined force, wherein the first predetermined force is greater than a maximum force provided manually by a user.

6. The robotic surgical system of claim 4, wherein the disassembly feature is configured to apply the first predetermined force, wherein the portion of the surgical instrument includes a housing, wherein underapplication of the first predetermined force or overapplication of the first predetermined force does not release the housing.

7. The robotic surgical system of claim 4, wherein the disassembly feature is configured to apply a second predetermined force, a second predetermined motion, or second predetermined task independent from the first predetermined force, the first predetermined motion, or the first predetermined task to disconnect at least the portion of the surgical instrument in response to the instructions from the controller.

8. The robotic surgical system of claim 4, further comprising a second tool that includes a second disassembly feature configured to apply a second predetermined force, a second predetermined motion, or second predetermined task independent from the first predetermined force, the first predetermined motion, or the first predetermined task to disconnect at least the portion of the surgical instrument in response to the instructions from the controller.

9. The robotic surgical system of claim 1, further comprising a package, wherein the package is configured to receive the portion of the surgical instrument in response to the instructions from the controller.

10. The robotic surgical system of claim 9, further comprising a sealing device configured to seal the package after the portion of the surgical instrument is received by the package in response to the instructions from the controller.

11. The robotic surgical system of claim 1, wherein the tool includes an end effector configured to interact with tissue of the patient, wherein the disassembly feature includes the end effector.

12. The robotic surgical system of claim 1, wherein the surgical instrument includes an ultrasonic surgical instrument, wherein the ultrasonic surgical instrument includes an ultrasonic component, wherein the controller is configured to autonomously instruct the disassembly feature to disconnect the ultrasonic component from the ultrasonic surgical instrument.

13. The robotic surgical system of claim 1, wherein the sensor is configured to sense an area around the robotic surgical system.

14. The robotic surgical system of claim 1, wherein the controller is configured to perform at least one mechanical or electrical test on the surgical instrument to determine reusability of the surgical instrument.

15. The robotic surgical system of claim 1, further comprising:
(a) a base;
(b) a first robotic arm extending outwardly from the base, wherein the first robotic arm is operatively coupled with the surgical instrument; and
(c) a second robotic arm extending outwardly from the base, wherein the second robotic arm is coupled with the tool.

16. A robotic surgical system comprising:

(a) a base;

(b) a controller;

(c) a first robotic arm extending outwardly from the base;

(d) a surgical instrument configured to interact with a patient, wherein the surgical instrument is operatively coupled with the first robotic arm;

(e) a second robotic arm extending outwardly from the base; and (f) a tool operatively coupled with the second robotic arm, wherein the tool includes a disassembly feature configured to disconnect at least a portion of the surgical instrument from the robotic surgical system in response to instructions from the controller, wherein the disassembly feature includes an end effector having a clamp arm, wherein the clamp arm includes an arm configured to interact with tissue of the patient.

17. A method of disassembling a robotic surgical system, wherein the robotic surgical system includes a controller, first and second robotic arms, a surgical instrument, and a tool, wherein the first robotic arm is operatively coupled with the surgical instrument, wherein the tool is in communication with the controller, the method comprising:

(a) performing a mechanical test on the surgical instrument;

(b) communicating between the controller and the surgical instrument to thereby determine reusability of the surgical instrument based on a mechanical test; and (c) based on the determined reusability, disassembling a portion of the surgical instrument that is operatively coupled the first robotic arm using a disassembly feature of the tool that is operatively coupled second robotic arm.

18. The method of claim 17, wherein the disassembling further comprises autonomously applying a predetermined force, motion, or stroke to overcome a connection bias of the surgical instrument.

19. The method of claim 17, further comprising identifying the tool to perform the disassembly in response to instructions from the controller, and subsequently disassembling the portion of the surgical instrument in response to the instructions from the controller.

20. The method of claim 17, further comprising in response to instructions from the controller:

(a) inserting at least a portion of the surgical instrument into a package; and (b) sealing the package that contains the portion of the surgical instrument using a sealing apparatus.

* * * * *